United States Patent [19]
Li

[11] Patent Number: 5,954,057
[45] Date of Patent: Sep. 21, 1999

[54] SOFT TISSUE SUSPENSION CLIP, CLIP ASSEMBLY, EMPLACEMENT TOOL AND METHOD

[75] Inventor: Lehmann K. Li, Milford, Conn.

[73] Assignee: Li Medical Technologies, Inc., Shelton, Conn.

[21] Appl. No.: 09/064,794

[22] Filed: Apr. 22, 1998

Related U.S. Application Data

[63] Continuation of application No. 08/798,114, Feb. 12, 1997, abandoned.

[51] Int. Cl.$^6$ ............................. A61B 19/00; A61B 17/04
[52] U.S. Cl. ............................. 128/898; 128/778; 600/29; 600/37; 606/139; 606/148
[58] Field of Search .................................... 606/139, 148; 600/29, 37; 128/898, 778

[56] References Cited

U.S. PATENT DOCUMENTS

| | | |
|---|---|---|
| 1,454,550 | 5/1923 | Mabry . |
| 3,664,345 | 5/1972 | Dabbs et al. . |
| 4,813,407 | 3/1989 | Vogen ................................. 128/92 VZ |
| 5,037,021 | 8/1991 | Mills et al. ............................... 227/175 |
| 5,047,039 | 9/1991 | Avant et al. ............................. 606/148 |
| 5,112,344 | 5/1992 | Petros ....................................... 606/148 |
| 5,256,133 | 10/1993 | Spitz ......................................... 600/29 |
| 5,337,736 | 8/1994 | Reddy ....................................... 128/20 |
| 5,362,294 | 11/1994 | Seitzinger ................................. 600/37 |
| 5,439,467 | 8/1995 | Benderev et al. ....................... 606/139 |
| 5,544,664 | 8/1996 | Benderev et al. ....................... 128/898 |
| 5,611,515 | 3/1997 | Benderev et al. ....................... 128/898 |
| 5,649,940 | 7/1997 | Hart et al. ................................ 606/148 |
| 5,657,764 | 8/1997 | Coulter et al. ........................... 128/778 |

FOREIGN PATENT DOCUMENTS

| | | |
|---|---|---|
| 0002801 | 1/1897 | United Kingdom . |

OTHER PUBLICATIONS

Microvasive, Boston Scientific Corporation, "Vesica™ Percutaneous Bladder Neck Suspension Kit", 435161–01 Rev. A, pp. 2–15, plus front and back pages.

Beckman, "Laparoscopic Techniques Show Promise In Correcting Urinary Stress Incontinence", Urogynecology.

Kammerer–Doak et al., "What's New in Gynecology and Obstetrics", Journal of the American College of Surgeons, Feb. 1996, vol. 182.

Flanigan, "What's New in Urology". From Dept. of Urology, Loyola University Medical Center, Maywood, Ill.

M–D–D–I Reports—"The Gray Sheet", "Pelvic Floor Electrical Stimulation Reduces Stress Incontinence", F–D–C Reports, Inc., Mar. 18, 1996, pp. 12–14.

Microvasive, Boston Scientific Corporation, "PBNS Percutaneous Bladder Neck Stabilization Technique", 1996.

Microvasive, Boston Scientific Corporation, "Instrumentation for less invasive treatment of female incontinence", 1996.

Benderev, "A Modified Percutaneous Outpatient Bladder Neck Suspension System", The Journal Of Urology, vol. 152, pp. 2316–2320, Dec. 1994.

Mascio, "Therapy Of Urinary Stress Incontinence In Women Using Mitek® GII Anchors", Mitek Surgical Products, Inc., 1993.

Scheuer, "The Modified Pereyra Bladder Neck Suspension Procedure Using Mitek® GII Anchors", Mitek Surgical Products, Inc., 1993.

Krantz, "The Marshall–Marchetti–Krantz Surgical Technique for Urinary Stress Incontinence", Mitek Surgical Products, Inc., 1993.

Microvasive, Boston Scientific Corporation, "ISS In Situ Sling Technique", 1996.

*Primary Examiner*—Gary Jackson
*Attorney, Agent, or Firm*—Pandiscio & Pandiscio

[57] ABSTRACT

A suspension clip assembly for suspending soft tissue from an appropriate bodily support structure, wherein the suspension clip assembly includes a suspension clip having a pointed structure for penetrating the soft tissue. The suspension clip assembly further includes a suspension strap mounted at a distal end thereof to the clip, the suspension strap being adapted so that a proximal end of the strap can be attached to the bodily support structure.

7 Claims, 18 Drawing Sheets

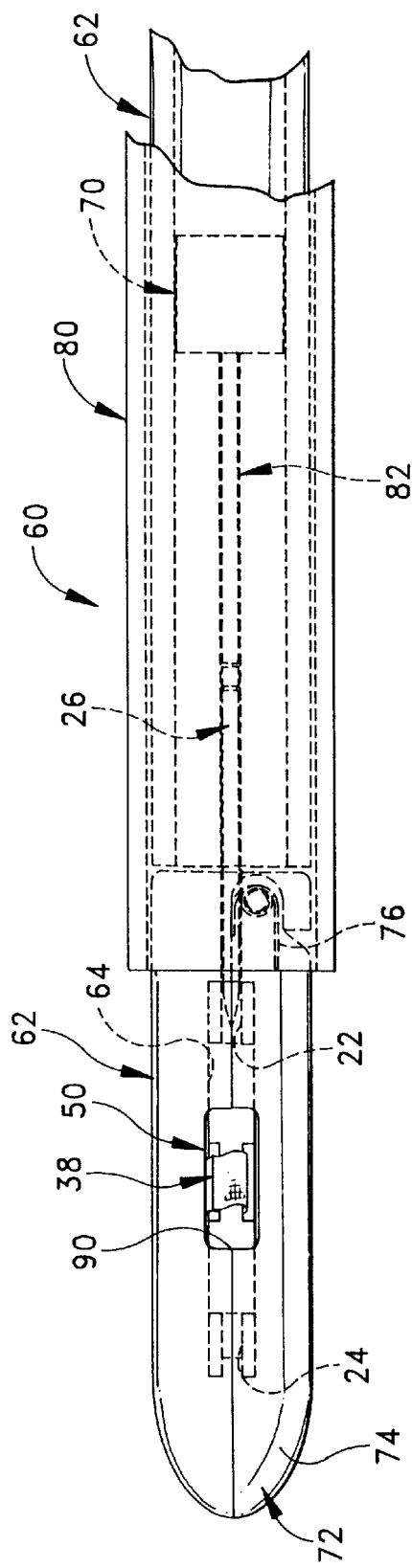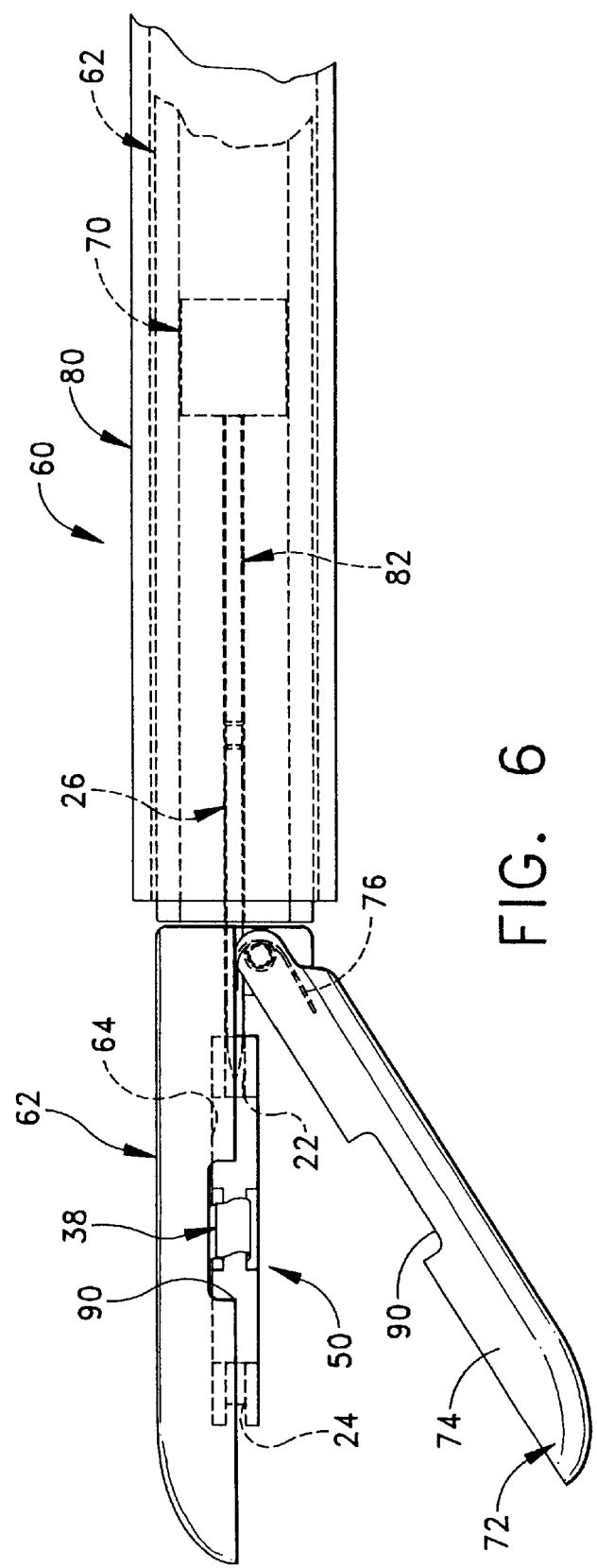

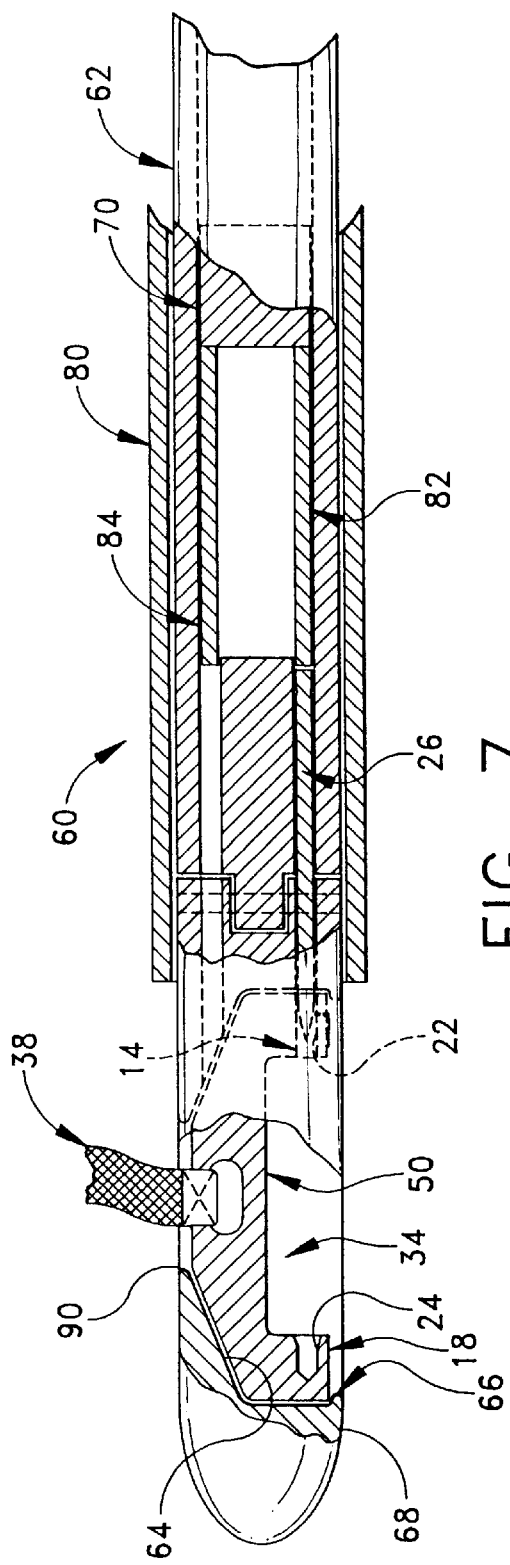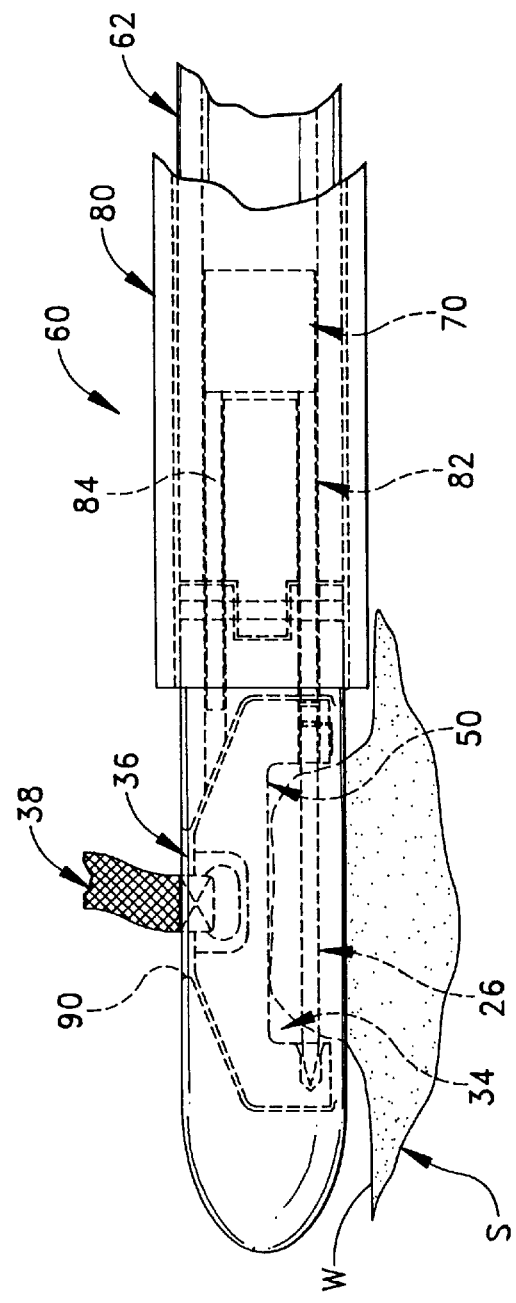

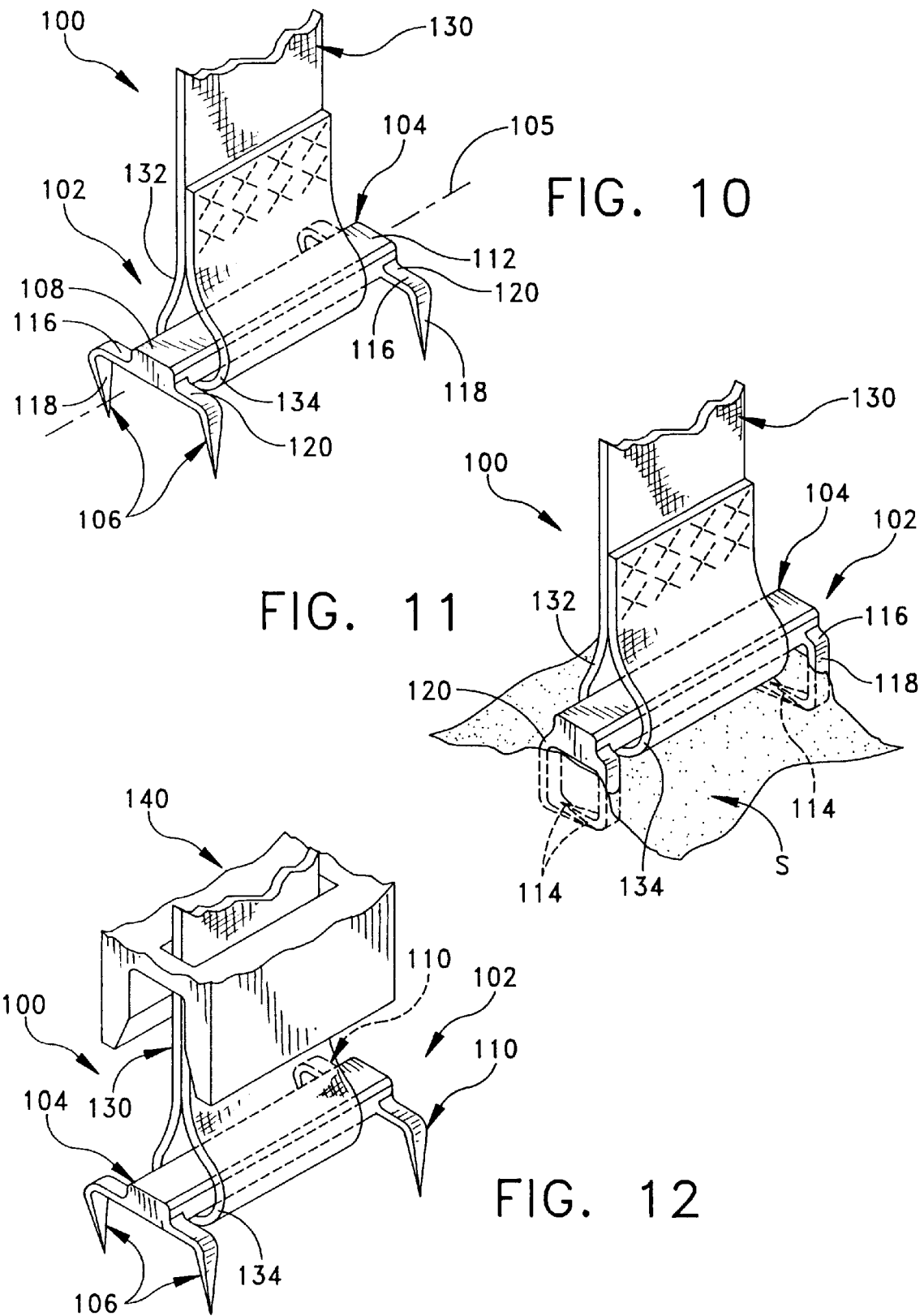

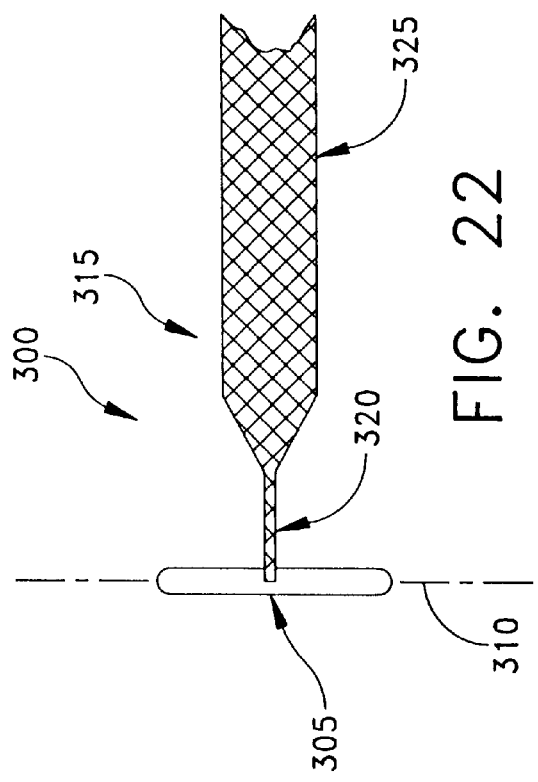
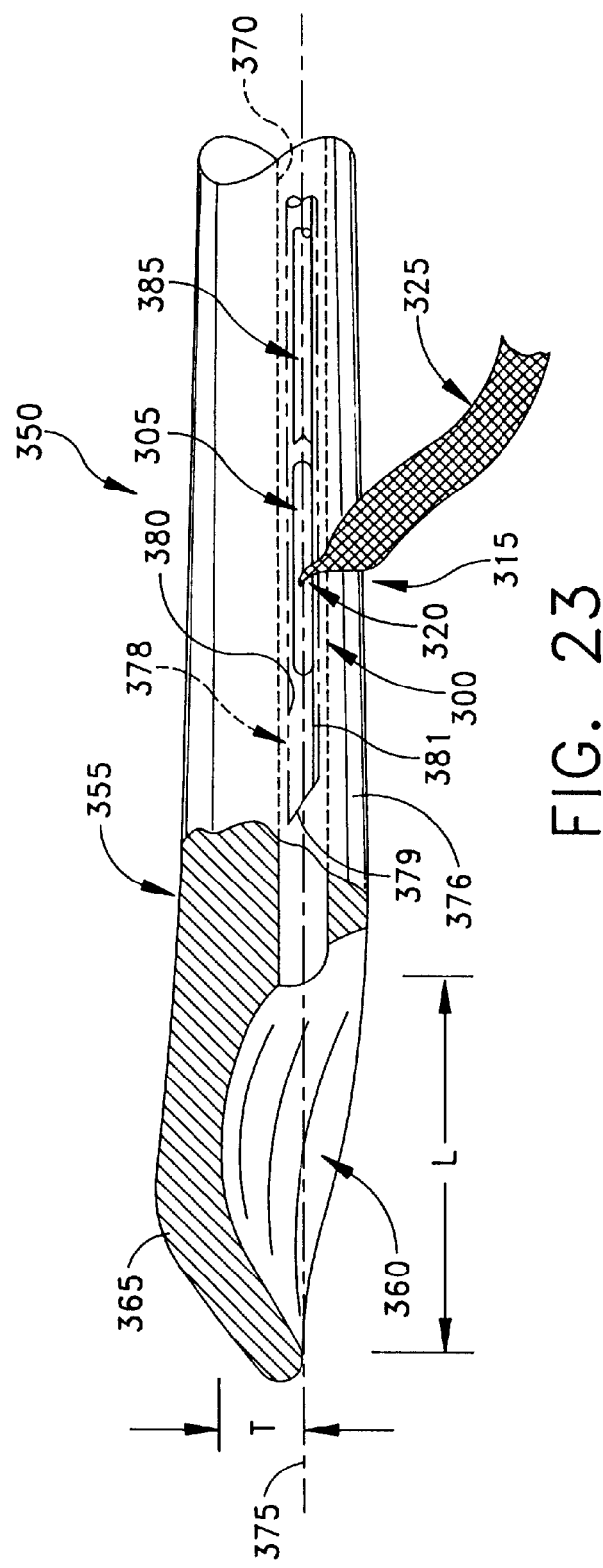
FIG. 22
FIG. 23

SOFT TISSUE SUSPENSION CLIP, CLIP ASSEMBLY, EMPLACEMENT TOOL AND METHOD

This is a continuation of U.S. patent application Ser. No. 08/798,114, filed Feb. 12, 1997, now abandoned by Lehmann K. Li for SOFT TISSUE SUSPENSION CLIP, CLIP ASSEMBLY, EMPLACEMENT TOOL AND METHOD.

FIELD OF THE INVENTION

This invention relates to surgical devices and procedures in general, and more particularly to devices and methods for suspending soft tissue in humans.

BACKGROUND OF THE INVENTION

In many situations it may be desirable or necessary to suspend soft tissue in humans. For example, in some circumstances it may be necessary to form a sling so as to suspend an internal organ from an appropriate bodily support structure, e.g., a skeletal structure, tissue, a prosthesis, etc. This may be required because that organ's normal support tissue has degenerated, or because that organ must be repositioned for some other anatomical reason. For example, it may be necessary to lift that organ away from some other shifting organ so as to avoid the formation of adhesions.

In one common situation, it is known that a sling can be used to lift intestines away from other anatomical structures so as to minimize the formation of adhesions within the abdominal cavity.

In another situation, suture can be used to raise a prolapsed (i.e., sagging) uterus.

Also, in plastic surgery, there arise situations in which suture is used to suspend tissue.

In another common situation, it is known that certain types of incontinence can be eliminated in women by lifting the bladder neck toward the pubic bone. Typically, the bladder neck is suspended in this lifted position by a plurality of sutures which are looped beneath the bladder neck and fixed to an anchor set in the pubic bone.

In some situations the soft tissue is supported by passing a suture directly through the soft tissue. Unfortunately, in such situations the suture may be difficult to set in the tissue due to space limitations. Also, it can be difficult for a surgeon to be consistent with respect to the amount of tissue grasped by the suture, particularly where suturing is undertaken laparoscopically, with relatively poor visualization and limited space. Unfortunately, if the "bite" taken by the suture is insufficient, the suture may tear through the tissue and fail. On the other hand, if the "bite" taken by the suture is too great, the suture may penetrate into underlying structure which may need to be avoided, e.g., a critical structure or a non-sterile region. Furthermore, the soft tissue may tend to "bunch up" around the suture as the suture is lifted upward to support the tissue. Also, even when properly set, the relatively narrow suture may tend to cut into the soft tissue as the suture is lifted upward, since the suture provides a relatively small surface area for bearing the load of the soft tissue.

There is thus a need for clips and/or clip emplacement tools which assist the surgeon in grasping the same amount of tissue time after time, the amount each time being sufficient to ensure good retention and minimize ripping through the tissue. There is further a need for a clip assembly which, with time, enhances rather than weakens the clip-to-tissue connection.

Because of the limited visualization and space available in such operations, surgeons must make a best estimate as to the amount of tension to be placed on the suspension strap. If too little tension is applied, the tissue sought to be lifted will be lifted too little and, in due course, settle back down to or near its original position. At the end of the suspension procedure, the tension usually is checked. At times, it is deemed important to increase the tension before closing, requiring that the upper end of the suspension assembly be re-worked before closing. On other occasions, it is only after completion of the operation and passage of time that it becomes known that the tension has not held adequately. In such instances the procedure must be repeated end-to-end.

Accordingly, there is a need for a suspension system in which the suspension tension may be readily adjusted to permit last-minute "fine-tuning" before closure and to permit a subsequent change in tension by attention only to one end of the suspension strap.

OBJECTS OF THE INVENTION

Accordingly, one object of the present invention is to provide a soft tissue suspension clip for use in suspending soft tissue from an appropriate bodily support structure.

Another object of the present invention is to provide a soft tissue suspension clip assembly comprising a suspension clip for attachment to the soft tissue which is to be supported, and a strap attached to the suspension clip, wherein the strap is adapted to be fixed at a selected length to an appropriate bodily support structure.

Still another object of the present invention is to provide a tool for emplacement of the soft tissue suspension clip assembly.

Yet another object of the present invention is to provide a method for suspending soft tissue from an appropriate bodily support structure.

A further object of the present invention is to provide a tissue suspension clip and/or emplacement tool which facilitates grasping of substantially the same amount of tissue each time used.

A still further object of the invention is to provide a suspension clip assembly which, through adhesion, increases the attachment of the clip to tissue over time.

A still further object of the invention is to provide a clip assembly and method which facilitate fine-tuning of tension on the suspension strap just prior to closing and also permit subsequent adjustment of tension at the upper end of the strap without having to disturb the lower end of the strap.

SUMMARY OF THE INVENTION

These and other objects of the present invention are addressed by the provision and use of a novel soft tissue suspension clip comprising a rigid elongated base block having a longitudinal axis. A first leg extends from a first end of the base block substantially normal to the base block axis, and a second leg extends from a second end of the base block substantially normal to the base block axis. The second leg is parallel to the first leg. A first aperture extends through the first leg and a second aperture extends at least partially through the second leg. The second aperture is aligned with the first aperture. A needle is adapted for movement through the first aperture, through soft tissue disposed between the first and second legs, and into the second aperture, with the needle being disposed in the first and second apertures so as to extend substantially parallel to the base block's longitudinal axis. A connector structure on the base block receives and retains a suspension strap.

The objects of the present invention are still further addressed by the provision and use of a novel soft tissue suspension clip assembly comprising a rigid elongated base block having a longitudinal axis, first and second legs extending, respectively, from first and second ends of the base block, with the first and second legs extending substantially normal to the base block's longitudinal axis, and first and second apertures extending, respectively, through the first and second legs, with the first and second apertures being aligned with one another. A needle is adapted to be disposed in the apertures so that it extends substantially parallel to the base block's longitudinal axis. A suspension strap is fixed to the base block and extends therefrom.

The objects of the present invention are still further addressed by the provision and use of a novel tool for emplacement of a soft tissue suspension clip assembly of the sort having an elongated rigid base portion and first and second legs extending normally to the base portion, wherein the first and second legs have aligned apertures formed therein, and wherein a needle is disposed in one of the apertures. The tool comprises an elongated tubular member having a compartment formed therein for receiving and retaining the suspension clip assembly, the tubular member having a first opening in an outer wall thereof communicating with the compartment so as to expose the suspension clip's legs. A pusher member is slidably movable in the tubular member and engageable with the needle so as to drive the needle into the other of the apertures, such that the needle is disposed in both of the apertures and extends through any intervening soft tissue.

The objects of the present invention are further addressed by the provision and use of a novel method for suspending soft tissue from an appropriate bodily support structure, the method comprising the steps of (i) providing a soft tissue suspension clip assembly comprising a soft tissue suspension clip having penetrating means thereon for penetrating soft tissue and a suspension strap fixed to the suspension clip and extending therefrom; (ii) placing the soft tissue suspension clip on a wall of the soft tissue; (iii) driving the penetrating means into the soft tissue so as to secure the suspension clip assembly to the soft tissue; (iv) drawing the suspension strap selectively taut so as to draw the soft tissue toward an appropriate bodily support structure; and (v) fixing a proximal portion of the strap to the support structure so as to suspend the soft tissue from the support structure.

The objects of the present invention are still further addressed by the provision and use of a novel soft tissue suspension clip comprising a rigid elongated base block having a longitudinal axis, a first pair of legs extending from a first end of the base block substantially normal to the base block axis, the legs of the first pair of legs being pointed at free ends thereof, and a second pair of legs extending from a second end of the base block substantially normal to the base block axis, the legs of the second pair of legs being pointed at free ends thereof, the legs of each of the pairs of legs being adapted to pierce soft tissue and being bendable toward one another so as to grip the tissue.

The objects of the present invention are further addressed by the provision and use of a novel suspension clip assembly comprising a rigid elongated base block having a longitudinal axis, a first pair of legs extending from a first end of the base block substantially normal to the base block axis, the legs of the first pair of legs being pointed at free ends thereof, and a second pair of legs extending from a second end of the base block substantially normal to the base block axis, the legs of the second pair of legs being pointed at free ends thereof, the legs of each of the pairs of legs being adapted to pierce soft tissue and being bendable toward one another so as to grip the tissue, and a suspension strap fixed to the base block and extending therefrom.

The objects of the present invention are still further addressed by an emplacement tool for emplacement of a soft tissue suspension clip assembly comprising a clip having a rigid base portion and first and second pairs of legs extending therefrom, the legs of each of the pairs of legs being pointed at free ends thereof to pierce soft tissue and bendable towards one another so as to grip the tissue, and a suspension strap extending from the base portion, the tool comprising a shaft having a distal end, the distal end defining a pocket for receiving the base portion of the suspension clip assembly and a distal portion of the strap, the shaft defining a passageway lengthwise thereof extending from the pocket and adapted to receive the strap extending from the base portion, and the shaft defining cam surfaces engageable with the legs and adapted to urge the pointed ends of the legs into tissue and to bend each of the legs toward another of the legs so as to grip the tissue.

The objects of the present invention are also addressed by the provision and use of a novel method for effecting suspension of soft tissue from an appropriate bodily support structure, the method comprising the steps of (i) providing a suspension clip assembly comprising a suspension clip having a rigid base portion, first and second pairs of legs extending from the base portion, the legs being pointed at distal ends thereof and bendable each toward another of the legs, and a suspension strap extending from the suspension clip; (ii) placing the suspension clip assembly adjacent a wall of the soft tissue; (iii) driving the pointed ends of the suspension clip's legs into the soft tissue; (iv) bending the legs of each of the pairs of legs toward each other so as to grip the soft tissue in the suspension clip; (v) drawing the strap selectively taut; and (vi) fixing a proximal portion of the strap to an appropriate bodily support structure, whereby to draw the soft tissue toward that support structure.

The objects of the present invention are also addressed by the provision and use of a novel suspension clip assembly comprising an elongated, relatively rigid body having a longitudinal axis, and an elongated, relatively flexible suspension strap attached to the body, the suspension strap comprising a first distalmost portion formed out of a relatively flexible material, and a second, proximalmost portion preferably formed out of a mesh material, the body being attached to the first, distalmost portion of the suspension strap so that (i) the first, distalmost portion of the suspension strap normally extends substantially perpendicular to the longitudinal axis of the body, and (ii) the first, distalmost portion of the suspension strap may be bent so that at least some of the first, distalmost portion of the suspension strap extends substantially parallel to the longitudinal axis of the body, whereby when the body is driven through soft tissue with at least some of the first, distalmost portion of the suspension strap extending substantially parallel to the longitudinal axis of the body, the first, distalmost portion of the suspension strap will thereafter permit the body to turn so as to restore the original perpendicular orientation of the first, distalmost portion of the suspension strap relative to the body.

The objects of the present invention are also addressed by the provision and use of a novel emplacement tool for emplacement of a suspension clip assembly of the sort comprising an elongated, relatively rigid body having a longitudinal axis, and an elongated, relatively flexible suspension strap attached to the body, the suspension strap comprising a first distalmost portion formed out of a relatively flexible material, and a second, proximalmost portion preferably formed out of a mesh material, the body being attached to the first, distalmost portion of the suspension strap so that (i) the first, distalmost portion of the suspension strap normally extends substantially perpendicular to the longitudinal axis of the body, and (ii) the first, distalmost portion of the suspension strap may be bent so that at least some of the first, distalmost portion of the suspension strap extends substantially parallel to the longitudinal axis of the body, whereby when the body is driven through a piece of soft tissue with at least some of the first, distalmost portion of the suspension strap extending substantially parallel to the longitudinal axis of the body, the first, distalmost portion of the suspension strap will thereafter permit the body to turn so as to restore the original perpendicular orientation of the first, distalmost portion of the suspension strap relative to the body. The emplacement tool comprises a housing having a pre-curved pocket adjacent its distal end, and a passageway extending through the housing and opening on the pre-curved pocket. The emplacement tool also comprises an elongated shaft slidably disposed in the housing, the elongated shaft terminating in a pointed distal end, and the elongated shaft having (i) a bore extending lengthwise therethrough, and (ii) a radial slot extending along the length of the bore and communicating with the region exterior of the shaft, the bore being sized so as to slidably receive the body of the suspension clip assembly when that body is positioned lengthwise in the bore, and the slot being sized so as to permit the suspension strap to pass from the body disposed in the bore to the region exterior of the shaft. The emplacement tool also comprises a pusher slidably disposed in the bore and adapted to push the body of the suspension clip assembly along the bore so as to expel the body of the suspension clip assembly from the distal end of the shaft.

The objects of the present invention are also addressed by the provision and use of a novel method for effecting suspension of soft tissue from an appropriate bodily support structure, the method comprising the steps of (1) providing a suspension clip assembly comprising an elongated, relatively rigid body having a longitudinal axis, and an elongated, relatively flexible suspension strap attached to the body, the suspension strap comprising a first distalmost portion formed out of a relatively flexible material, and a second, proximalmost portion formed out of a mesh material, the body being attached to the first, distalmost portion of the suspension strap so that (i) the first, distalmost portion of the suspension strap normally extends substantially perpendicular to the longitudinal axis of the body, and (ii) the first, distalmost portion of the suspension strap may be bent so that at least some of the first, distalmost portion of the suspension strap extends substantially parallel to the longitudinal axis of the body, whereby when the body is driven through soft tissue with at least some of the first, distalmost portion of the suspension strap extending substantially parallel to the longitudinal axis of the body, the first, distalmost portion of the suspension strap will thereafter permit the body to turn so as to restore the original perpendicular orientation of the first, distalmost portion of the suspension strap relative to the body; (2) passing the body of the suspension clip assembly through the soft tissue so that the body resides in the far side of the soft tissue and the suspension strap extends through the soft tissue; and (3) fixing the second, proximalmost portion of the suspension strap to an appropriate bodily support structure, whereby to draw the soft tissue toward the bodily support structure.

The objects of the present invention are further addressed by the provision and use of a novel suspension clip assembly comprising a first elongated relatively rigid body having a first longitudinal axis, a second elongated relatively rigid body having a second longitudinal axis, an elongated relatively flexible suspension strap attached to the first and second bodies, the suspension strap comprising first and second distalmost portions of relatively flexible material, and a proximalmost portion of a mesh material, the first body being attached to the first distalmost portion of the suspension strap such that (i) the first distalmost portion of the suspension strap normally extends substantially perpendicular to the first longitudinal axis, and (ii) the first distalmost portion of the suspension strap is bendable so that at least some of the first distalmost portion of the suspension strap is extendible substantially parallel to the first longitudinal axis, the second body being attached to the second distalmost portion of the suspension strap such that (i) the second distalmost portion of the suspension strap normally extends substantially perpendicular to the second longitudinal axis, and (ii) the second distalmost portion of the suspension strap is bendable so that at least some of the second distalmost portion of the suspension strap is extendible substantially parallel to the second longitudinal axis, whereby when the first and second bodies are driven through soft tissue with at least some of the first and second distalmost portions of the suspension strap extending substantially parallel to the first and second longitudinal axes, respectively, the first and second distalmost portions of the suspension strap permit the first and second bodies, respectively, to turn so as to restore the original perpendicular orientation of the first distalmost portion of the suspension strap relative to the first body and the second distalmost portion of the suspension strap relative to the second body.

The objects of the present invention are also addressed by the provision and use of a novel emplacement tool for emplacement of a suspension clip assembly of the sort comprising a first elongated relatively rigid body having a first longitudinal axis, a second elongated relatively rigid body having a second longitudinal axis, an elongated relatively flexible suspension strap attached to the first and second bodies, the suspension strap comprising first and second distalmost portions of relatively flexible material, and a proximalmost portion of a mesh material, the first body being attached to the first distalmost portion of the suspension strap such that (i) the first distalmost portion of the suspension strap normally extends substantially perpendicular to the first longitudinal axis, and (ii) the first distalmost portion of the suspension strap is bendable so that at least some of the first distalmost portion of the suspension strap is extendible substantially parallel to the first longitudinal axis, the second body being attached to the second distalmost portion of the suspension strap such that (i) the second distalmost portion of the suspension strap normally extends substantially perpendicular to the second longitudinal axis, and (ii) the second distalmost portion of the suspension strap is bendable so that at least some of the second distalmost portion of the suspension strap is extendible substantially parallel to the second longitudinal axis, whereby when the first and second bodies are driven through soft tissue with at least some of the first and second distalmost portions of the suspension strap extending substantially parallel to the first and second longitudinal axes, respectively, the first and second distalmost portions of the suspension strap permit the first and second bodies, respectively, to turn so as to restore the original perpendicular orientation of the first distalmost portion of the suspension strap relative to the first body and the second distalmost portion of the suspension strap relative to the second body, the emplacement tool comprising: a housing having a first housing portion having a first curved pocket adjacent a distal end of the first housing portion, and a second housing portion having a second curved pocket adjacent a distal end of the second housing portion, a first passageway extending through the first housing portion and opening into the first curved pocket, and a second passageway extending through the second housing portion and opening into the second curved pocket; a first elongated shaft slidably disposed in the first housing portion, the first elongated shaft terminating in a first pointed distal end, the first elongated shaft having (i) a first bore extending lengthwise therethrough, and (ii) a first radial slot extending along the length of the first bore and communicating with a region exterior of the shaft, the first bore being sized so as to slidably receive the first body of the suspension clip assembly, the first slot being sized to permit the suspension strap to pass from the first body disposed in the first bore to the region exterior of the first shaft; a second elongated shaft slidably disposed in the second housing portion, the second elongated shaft terminating in a second pointed distal end, the second elongated shaft having (i) a second bore extending lengthwise therethrough, and (ii) a second radial slot extending along the length of the second bore and communicating with a region exterior of the second shaft, the second bore being sized so as to slidably receive the second body of the suspension clip assembly, the second slot being sized so as to permit the suspension strap to pass from the second body disposed in the second bore to a region exterior of the second shaft, and a first pusher slidably disposed in the first bore and adapted to push the first body of the suspension clip assembly along the first bore to expel the first body of the suspension clip assembly from the distal end of the first shaft, and a second pusher slidably disposed in the second bore and adapted to push the second body of the suspension clip assembly along the second bore to expel the second body of the suspension clip assembly from the distal end of the second shaft.

The objects of the present invention are still further addressed by the provision and use of a novel method for effecting suspension of soft tissue from an appropriate bodily support structure, the method comprising the steps of providing a suspension clip assembly comprising a first elongated relatively rigid body having a first longitudinal axis, a second elongated relatively rigid body having a second longitudinal axis, an elongated relatively flexible suspension strap attached to the first and second bodies, the suspension strap comprising first and second distalmost portions of relatively flexible material, and a proximalmost portion of a mesh material, the first body being attached to the first distalmost portion of the suspension strap such that (i) the first distalmost portion of the suspension strap normally extends substantially perpendicular to the first longitudinal axis, and (ii) the first distalmost portion of the suspension strap is bendable so that at least some of the first distalmost portion of the suspension strap is extendible substantially parallel to the first longitudinal axis, the second body being attached to the second distalmost portion of the suspension strap so that (i) the second distalmost portion of the suspension strap normally extends substantially perpendicular to the second longitudinal axis, and (ii) the second distalmost portion of the suspension strap is bendable so that at least some of the second distalmost portion of the suspension strap is extendible substantially parallel to the second longitudinal axis, whereby when the first and second bodies are driven through soft tissue with at least some of the first and second distalmost portions of the suspension strap extending substantially parallel to the first and second longitudinal axes, respectively, the first and second distalmost portions of the suspension strap permit the first and second bodies, respectively, to turn so as to restore the original perpendicular orientation of the first distalmost portion of the suspension strap relative to the first body and the second distalmost portion of the suspension strap relative to the second body, passing the bodies of the suspension clip assembly through the soft tissue such that the bodies reside in a far side of the soft tissue and the suspension strap extends through the soft tissue, and fixing the proximalmost portion of the suspension strap to the bodily support structure, whereby to draw the soft tissue toward the support structure.

The above and other objects of the present invention are further addressed by the provision and use of a first suspension clip comprising a rigid base portion, legs extending in a first direction from the base portion and forming in conjunction with the base portion a tissue capture zone. The clip further includes a selected one of (i) distal portions of the legs, and (ii) penetration means extendible through the legs, moveable into the tissue capture zone to penetrate the tissue in the capture zone. The base portion and the selected one of the leg distal portions and the penetration means spaced from the base portion, define therebetween a shape and volume of tissue capturable by the first suspension clip. The first suspension clip is thereby adapted to capture tissue of a shape and size substantially similar to tissue of a shape and size capturable by a second suspension clip of substantially similar shape and size as the first suspension clip.

The objects of the present invention are further addressed by the provision and use of a tool for emplacing a suspension clip adapted for being driven through tissue, the tool comprising a distal portion defining a pocket for receiving tissue to be suspended. The tool defines a bore extending proximally from the pocket and adapted to receive and retain a clip, and actuating means for driving the clip from the bore and through the tissue. The pocket and a hypothetical extension of the bore through the pocket define a volume substantially equal to a selected volume of tissue to be captured by the clip, such that in repeated use of the tool on a selected tissue, each clip emplaced by the tool is emplaced so as to capture a volume of the tissue substantially equal to volumes of tissue captured by other clips emplaced in the selected tissue by the tool.

The objects of the present invention are still further addressed by the provision and use of a suspension clip assembly comprising a suspension strap having a distal end and a proximal end, and a clip fixed to the distal end of the strap and adapted for attachment to tissue to be suspended. The suspension strap is of a mesh-like material, and the distal end of the strap is subject to adhesion to the tissue, and the proximal end of the strap is adapted for hanging on a pin extending from a support body part.

The objects of the present invention are still further addressed by the provision and use of a method for suspending a first internal body part from a second internal body part, the method comprising the steps of providing a suspension assembly including a suspension strap of a mesh structure and having distal and proximal ends, and a clip fixed to the distal end of the strap, attaching the clip to the first internal body part, extending the strap toward the second internal body part, and attaching the strap proximate the proximal end thereof to a pin previously fixed in the second internal body part by hanging the mesh structure on the pin. Optionally, tension on the strap readily may be adjusted by removing the strap from the pin and reattaching the strap to the pin by re-hanging the strap on the pin to produce an adjusted tension.

The objects of the present invention are also addressed by the provision and use of a suspension assembly for suspending soft tissue from a bodily support structure, the assembly comprising an attachment body adapted for attachment to the soft tissue; and a suspension strap having a proximal end and a distal end, the suspension strap being connected at the distal end thereof to the attachment body and extending therefrom, the suspension strap having a multiplicity of connectors disposed along a proximal portion lengthwise of the suspension strap, each of the connectors being adapted for connection to and removal from a fixture attached to the bodily support structure, whereby to provide for adjustable selection of a length of the suspension strap between the tissue and the fixture attached to the bodily support structure.

The objects of the present invention are also addressed by the provision and use of a method for effecting suspension of soft tissue from a bodily support structure, the method comprising the steps of providing a suspension assembly including an attachment body and a suspension strap connected to the attachment body and extending therefrom, the suspension strap having connectors thereon disposed along a proximal portion lengthwise of the suspension strap, attaching the body to the soft tissue, fixing a selected one of the suspension strap connectors to a fixture attached to the bodily support so as to draw the suspension strap selectively taut to draw the soft tissue toward the bodily support structure. The length of the suspension strap between the tissue and the bodily support structure is adjusted by detaching the selected one of the suspension strap connectors from the fixture and fixing a selected second of the suspension strap connectors to the fixture.

BRIEF DESCRIPTION OF THE DRAWINGS

These and other objects and features of the present invention will be more fully disclosed or rendered obvious by the following detailed description of the preferred embodiments of the invention, which are to be considered together with the accompanying drawings wherein like numbers refer to like parts, and further wherein:

FIG. 5 is a top plan of the distal end of one form of emplacement tool illustrative of an embodiment of the present invention;

FIG. 6 is a view similar to FIG. 5, but shows the emplacement tool in an "open" configuration, for the insertion and removal of the suspension clip assembly of FIG. 4;

FIG. 7 is a side elevational view, partly in section, of the distal end of the emplacement tool of FIG. 5 and suspension clip assembly of FIG. 4;

FIG. 8 is a side elevational view showing the suspension clip assembly of FIG. 7 engaging soft tissue;

FIG. 10 is a perspective view showing other forms of the suspension clip and the suspension clip assembly illustrative of alternative embodiments of the present invention;

FIG. 11 is a view similar to FIG. 10, but illustrative of the suspension clip engaging soft tissue;

FIG. 12 is a view similar to FIG. 10, and further illustrative of the distal end of an emplacement tool used for emplacement of the suspension clip shown in FIG. 10;

FIG. 22 is a side elevational view of a portion of another form of suspension clip assembly formed in accordance with the present invention;

FIG. 23 is a partial side view, partially in section, of the suspension clip assembly of FIG. 22 shown loaded in an appropriate emplacement tool;

DETAILED DESCRIPTION OF THE PREFERRED EMBODIMENTS

Figure 1:
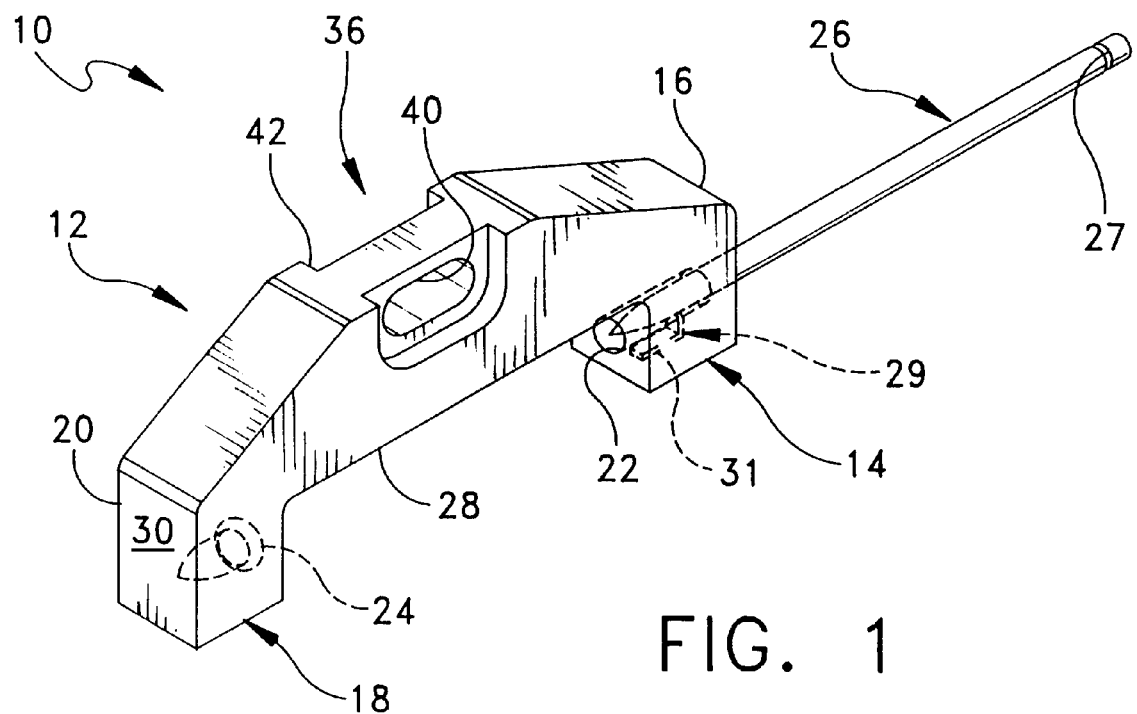
FIG. 1 is a perspective view of one form of suspension clip illustrative of an embodiment of the present invention.
Figure 2:
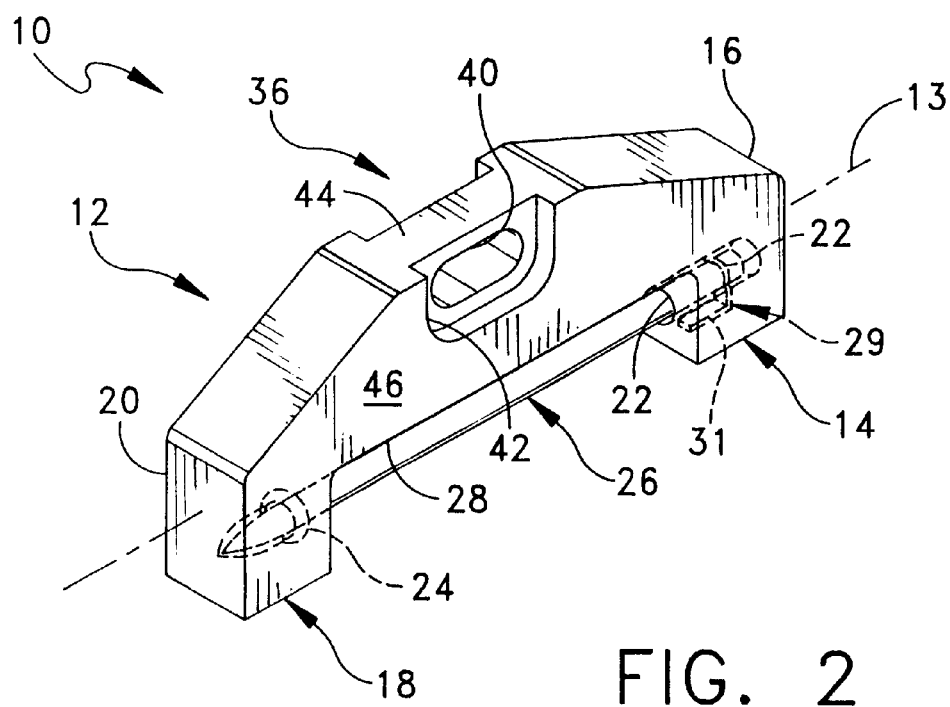
FIG. 2 is similar to FIG. 1, but shows the suspension clip in a different operating configuration.
Figure 3:
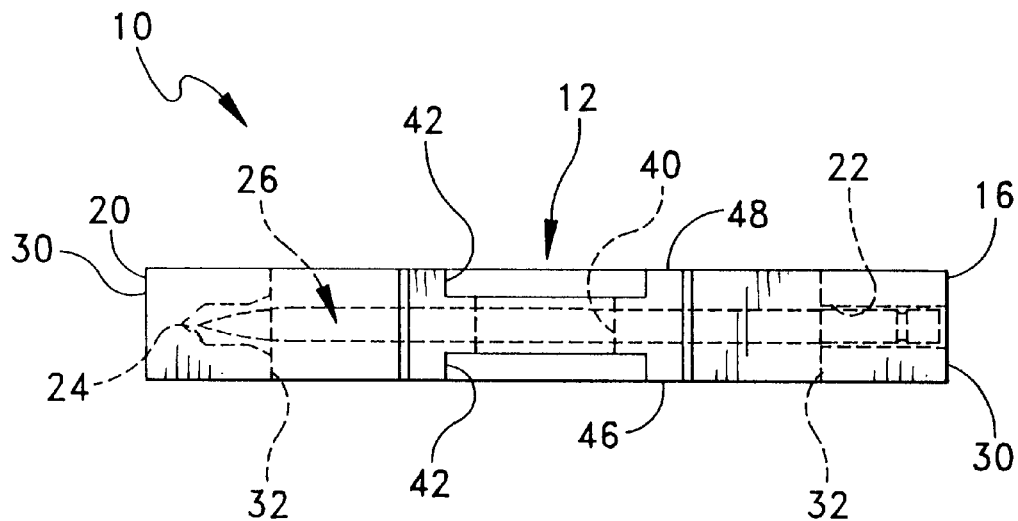
FIG. 3 is a top plan view of the suspension clip of FIG. 2.

Referring first to FIGS. 1–3, it will be seen that an illustrative suspension clip 10 includes a rigid elongated base block 12 having a longitudinal axis 13 (FIG. 2). A first leg 14 extends from a first end 16 of base block 12 in a direction substantially normal to longitudinal axis 13. A second leg 18 extends from a second end 20 of base block 12 in a direction substantially normal to longitudinal axis 13 and parallel to first leg 14.

A first aperture 22 extends through first leg 14, and a second aperture 24 extends at least partially through second leg 18. First aperture 22 and second aperture 24 are aligned with one another. First aperture 22 and second aperture 24 are also preferably aligned with the suspension clip's longitudinal axis 13.

Suspension clip 10 further includes a needle 26 which is adapted for movement through first aperture 22 and into second aperture 24. Needle 26 is of a length sufficient for simultaneous disposition of the needle in both first aperture 22 and second aperture 24, as shown in FIG. 2, wherein needle 26 is disposed substantially parallel to axis 13. Needle 26 is sharply pointed at its distal end, and is provided with an annular groove 27 (FIG. 1) adjacent its proximal end for receiving a locking flange member 29 mounted in first leg 14. Flange member 29 preferably is a portion of a leaf spring 31, or the like, adapted to snap into the needle's groove 27 so as to lock needle 26 in place.

Base block 12 includes an edge 28 which is planar and extends substantially parallel to the base block's longitudinal axis 13. First leg 14 and second leg 18 are provided with surfaces 30 and 32 (FIG. 4) which are disposed normal to edge 28. Edge 28 and surfaces 32 together define a recess or space 34 for receiving soft tissue therein, as will be discussed in further detail below. Apertures 22 and 24 are disposed so that needle 26 will extend parallel to, but spaced from, the base block's edge 28, such that needle 26 will penetrate soft tissue disposed in recess 34, as will also be discussed in further detail below.

The base block edge 28 and first and second leg surfaces 32 define a tissue capture zone. The base block edge 28 and the needle 26 define therebetween a shape and volume of tissue capturable by the clip 10, and which can be substantially duplicated by a second clip of similar size and shape as the clip 10.

Figure 4:
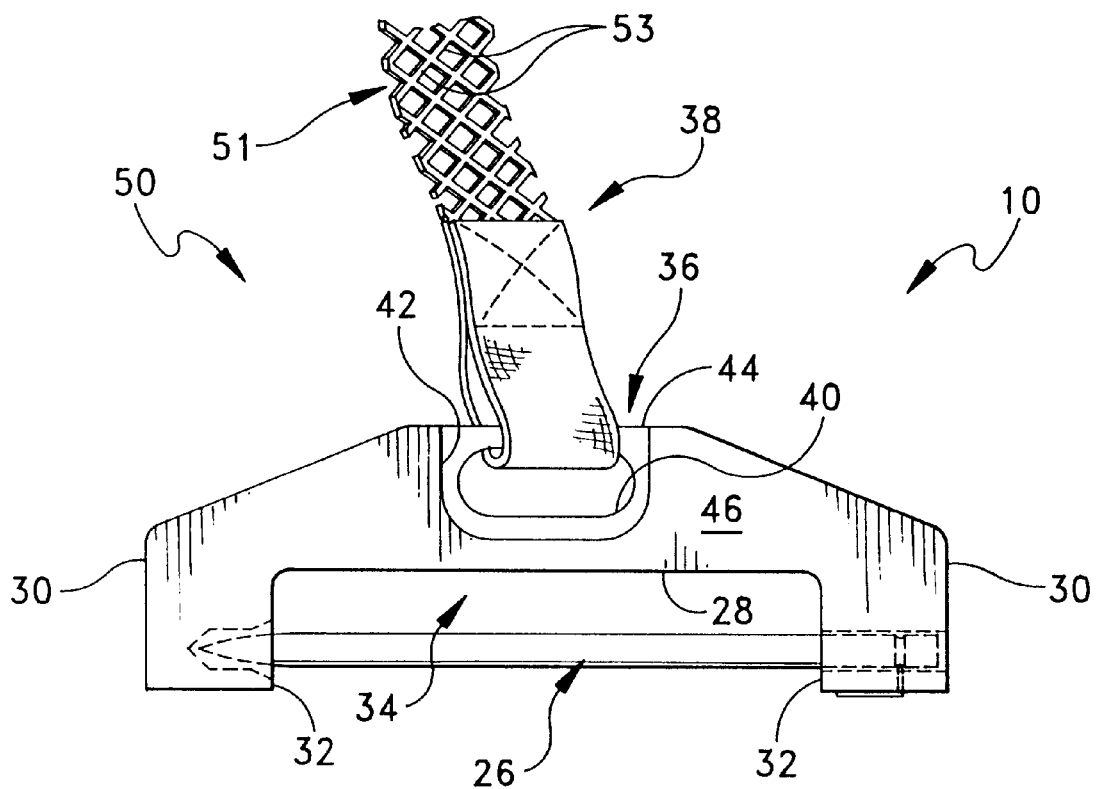
FIG. 4 is a side elevational view of one form of suspension clip assembly illustrative of a further embodiment of the invention.

Suspension clip 10 further includes a connector structure 36 for receiving and retaining a suspension strap 38, shown in FIG. 4. As illustrated, connector structure 36 may comprise a hole 40 extending through base block 12, normal to axis 13. The connector structure 36 may further include grooves 42 (FIG. 3) extending between the outboard ends of hole 40 and an edge 44 of base block 12. Grooves 42 receive portions of suspension strap 38, such that suspension strap 38 does not extend beyond side walls 46 and 48 of base block 12.

Suspension strap 38 may be permanently fixed to suspension clip 10 so as to provide a suspension clip assembly 50 (FIG. 4), which may be packaged as a unit. Suspension strap 38 is provided with a multiplicity of connectors 51, such as apertures 53, located at least near a proximal end 52 (FIG. 9) thereof, which connectors 51 are adapted for connection to means by which connection strap 38 is affixed to a bone B. Such means for connection of connection strap 38 to bone B may comprise, for example, a pin P (FIG. 9), or some other type of anchor. In particular, connection strap 38 may be of a web or mesh material so as to provide extensive selectivity relative to an aperture 53 to receive pin P. Alternatively, connector 51 may also comprise bead-like members (not shown) disposed serially along a strand and adapted to be received by a slotted flange (not shown) or a pair (not shown) of parallel pins P fixed in bone B.

Referring next to FIGS. 5–7, it will be seen that an illustrative emplacement tool 60 for emplacement of the above-described suspension clip assembly 50 comprises an elongated tubular member 62 having a compartment 64 formed therein for receiving and retaining suspension clip assembly 50. Tubular member 62 is provided with a first opening 66 (FIG. 7) in an outer wall 68 thereof. First opening 66 is in communication with compartment 64. Opening 66 exposes the suspension clip's two legs 14 and 18.

A pusher member 70 is slidably movable in tubular member 62 and is engageable with needle 26 so as to drive needle 26 from (i) an initial position in which the needle extends through only first aperture 22 (FIGS. 1 and 7), to (ii) a subsequent position in which the needle extends into second aperture 24 (FIGS. 2 and 8).

The emplacement tool's tubular member 62 is provided with locking means 72 for locking suspension clip 10 in compartment 64 and for releasing suspension clip 10 from compartment 64. As shown in FIG. 5, locking means 72 may comprise a hingedly mounted door 74, which door helps define a portion of compartment 64. Door 74 is biased by a spring 76 toward an open position, shown in FIG. 6.

Emplacement tool 60 is also provided with a sleeve 80 slidably mounted on tubular member 62. Sleeve 80 is movable by an operator to a first position (FIGS. 5 and 7) so as to cover at least a portion of door 74, whereby door 74 will be held closed against the bias of spring 76. Similarly, sleeve 80 is movable to a second position (FIG. 6) for unlocking door 74 and permitting opening of door 74 by spring 76. When door 74 is in this second position, suspension clip assembly 50 may be positioned in, or removed from, the engagement tool's compartment 64.

Pusher member 70 may include a drive pin 82 (FIGS. 5–8) engageable with needle 26 so as to drive needle 26 through the suspensions clip's first aperture 22, across its recess 34, and into its second aperture 24. Pusher member 70 may further include a guide pin 84 (FIGS. 7 and 8) to ensure proper orientation of pusher member 70 within tubular member 62.

Tubular member 62 is further provided with a second opening 90 (FIGS. 5–8) which is diametrically opposed to first opening 66. Second opening 90 is adapted to expose the suspension clip's strap connector structure 36, and to permit suspension strap 38 to pass therethrough, as will hereinafter be discussed in further detail.

In operation, suspension clip assembly 50 is first loaded into compartment 64 of tool 60. This is done by first moving sleeve 80 proximally so as to allow spring 76 to open door 74, and then fitting the suspension clip assembly into compartment 64. This is done while suspension clip assembly 50 is in the position shown in FIGS. 1 and 7, i.e., with needle 26 extending into only first aperture 22. Then sleeve 80 is moved distally so as to close door 74 and to lock suspension clip assembly 50 in compartment 64. Next, emplacement tool 60 is passed into the body and maneuvered so as to place the tool's first opening 66 adjacent to, and bearing into, a wall W of soft tissue (e.g., muscle) S (FIG. 8). As a result, the soft tissue S projects into the suspension clip's recess 34. Thereafter, distal movement of pusher member 70, e.g., by manual operation of a button or the like (not shown), causes pusher member 70 to engage needle 26 so as to drive needle 26 distally through first aperture 22, through the soft tissue S projecting between clip legs 14 and 18, and into second aperture 24, until the suspension clip's flange member 29 snaps into the needle's groove 27, whereby to lock the needle in place. As a result of the foregoing, clip assembly 50 will be securely attached to soft tissue S. By virtue of the fact that soft tissue S is maintained between the clip's legs 14 and 18, needle 26 will pass smoothly through soft tissue S, without "bunching up" of the tissue. Engagement tool 60 is then manipulated so as to open door 74, detach engagement tool 60 from suspension clip assembly 50, and withdraw tool 60 from the operative site.

Suspension strap 38 is then drawn, by means (e.g., forceps) not shown, toward the pin P previously inserted in an appropriate bodily support structure, i.e., a bone B. Suspension strap 38 is manipulated so as to assume the appropriate length and tension, and then is fixed to bone B by looping a selected aperture 53 in strap 38 over pin P. In the event a subsequent correction is required, strap 38 may be easily removed from pin P and simply re-attached to pin P with greater or lesser length or tension, as desired. By virtue of the fact that soft tissue S will be carried by the great majority of the length of needle 26, and by virtue of the fact that soft tissue S will lie smooth along the needle and not "bunch up", superior soft tissue suspension may be achieved.

Figure 9:
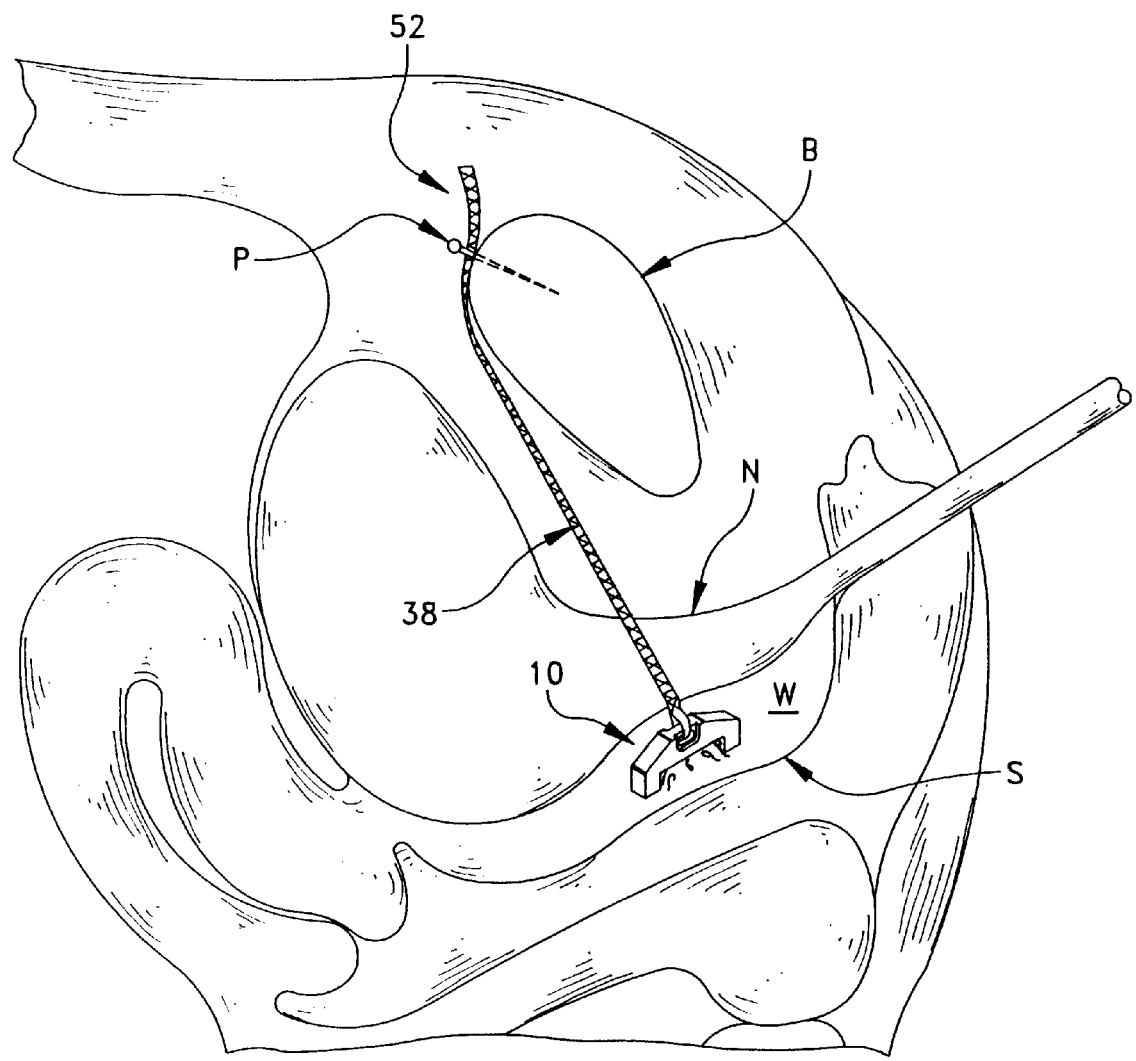
FIG. 9 is a diagrammatical view illustrating the suspension clip assembly of FIG. 4 being used to suspend soft tissue in a human female.

By way of specific example, in FIG. 9 the suspension clip 10 is shown deployed into a wall W of periurethral tissue S, whereby the periurethral tissue (and thereby a bladder neck portion N) may be lifted upward toward pubic bone B through a selected distance and under a selected tension. Such repositioning of bladder neck N may be effected so as to provide a remedy for incontinence in females.

Figure 9A:
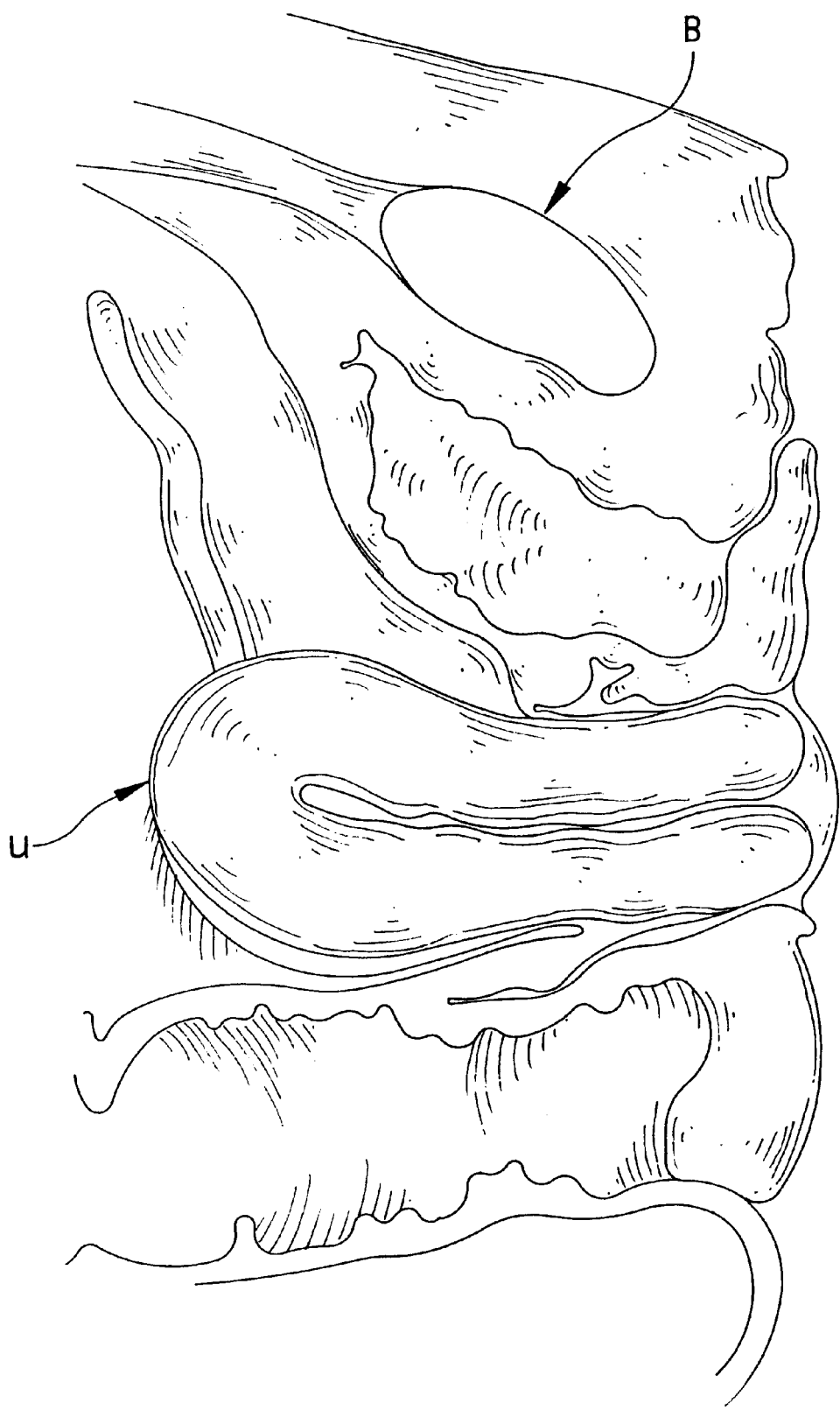
FIG. 9A is a diagrammatical view illustrating a prolapsed (i.e., sagging) uterus.
Figure 9B:
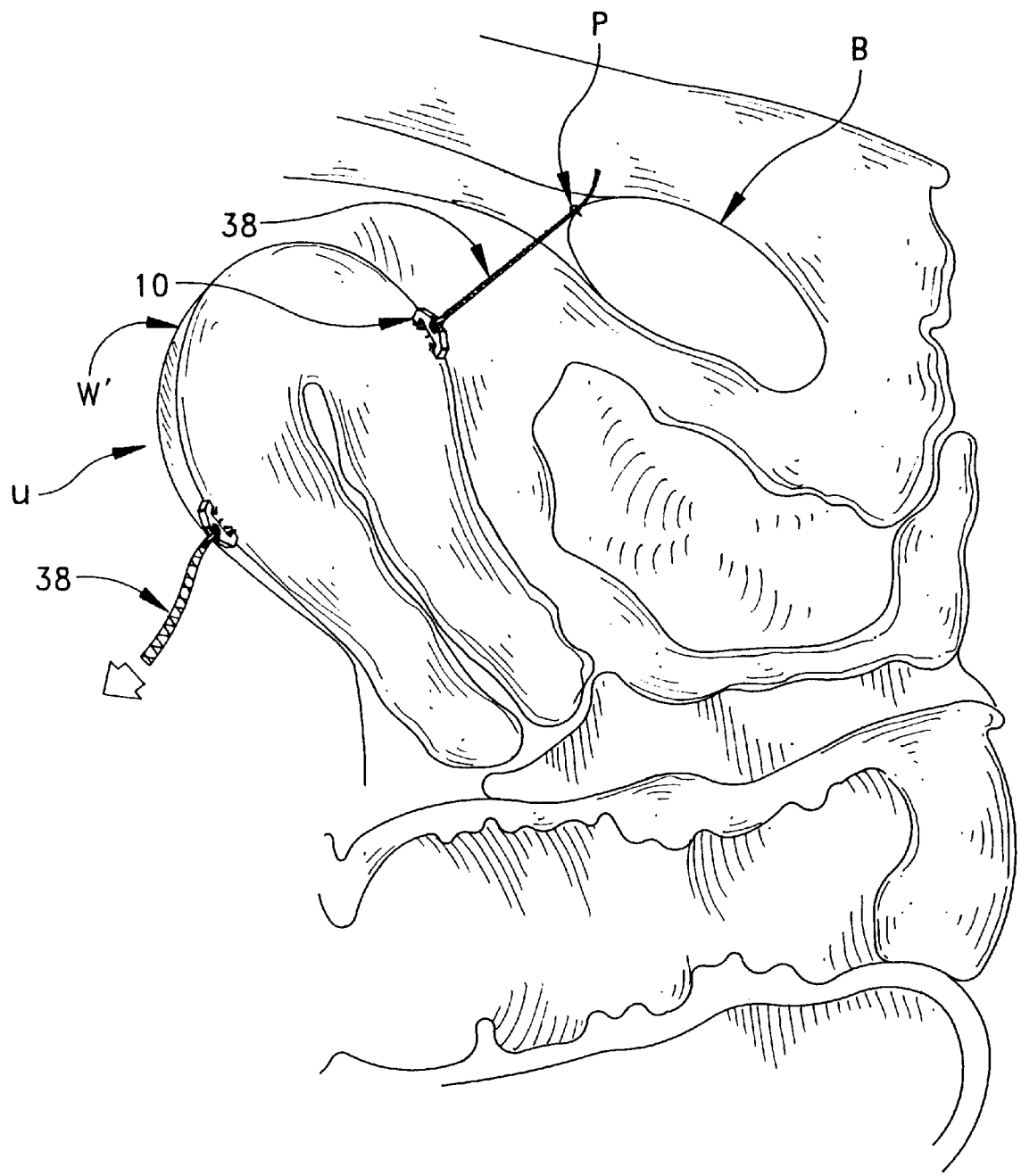
FIG. 9B is a diagrammatical view illustrating the suspension clip of FIG. 4 being used to suspend a prolapsed (i.e., sagging) uterus in a human female.

FIG. 9A shows a prolapsed (i.e., sagging) uterus U. FIG. 9B shows how suspension clip 10 may be deployed into a wall W' of a prolapsed uterus U, whereby the prolapsed uterus may be lifted back toward the pubic bone B and other bodily support structure (not shown) through a selected distance and under a selected tension.

Figure 9C:
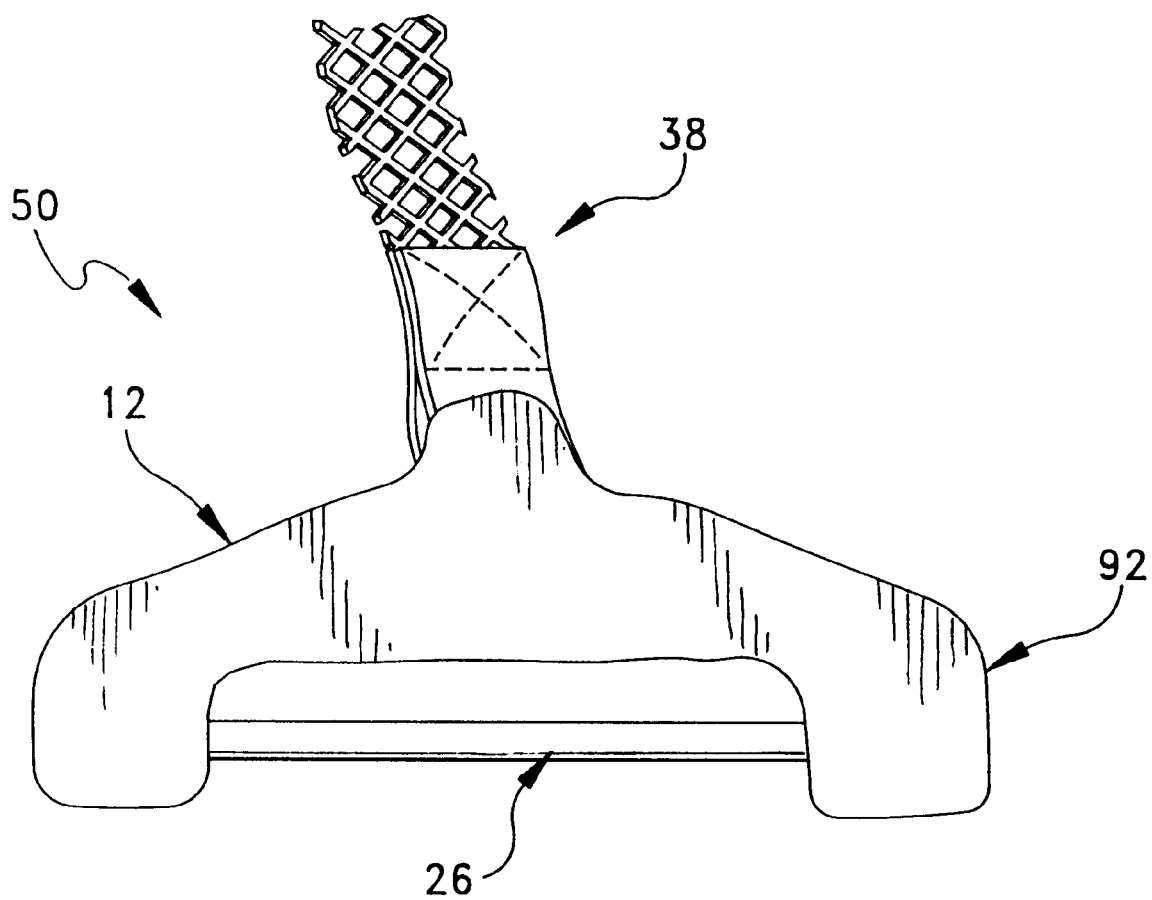
FIG. 9C is a schematic view showing an alternative form of suspension clip assembly.

Further, when strap 38 is of a mesh or web construction, or the like, the distal portions of strap 38 will, over time, become progressively adhered to the tissue by adhesion. Accordingly, the attachment of strap 38 to the suspended tissue becomes progressively stronger over time. To enhance the attachment of suspension clip assembly 50 to soft tissue S, mesh 92 might be wrapped around the exterior of the clip's base block 12 (FIG. 9C), so as to cause soft tissue S to adhere to mesh 92 during the healing process.

In FIGS. 10 and 11, there is shown an alternative embodiment of suspension clip assembly 100. Suspension clip assembly 100 comprises a suspension clip 102 having a rigid elongated base block 104 which extends along a longitudinal axis 105. A first pair of legs 106 extend from a first end 108 of base block 104 and a second pair of legs 110 extend from a second end 112 of base block 104. Each of the legs 106 and 110 is pointed at an end 114 thereof. Each of the legs 106 and 110 includes a first portion 116 which is directed outwardly from base block 104, substantially normal to the base block's longitudinal axis 105, and a second portion 118, which is a continuation of the leg's first portion 116, and which is directed substantially normal to the leg's first portion 116. Each of the legs 106 and 110 is bendable at a junction 120 where the leg's first portion 116 meets base block 104. Additional pairs of legs (not shown) may be provided, each additional pair being of the same structure and operating in the same manner as the afore-described first and second pair of legs 106, 110.

Suspension clip assembly 100 further includes a suspension strap 130 fixed to base block 104 of suspension clip 102. In a preferred embodiment, illustrated in FIGS. 10–15, an end 132 of suspension strap 130 is provided with a loop 134 extending around the suspension clip's base block 104 and disposed between the pairs of legs 106 and 110.

Figure 13:
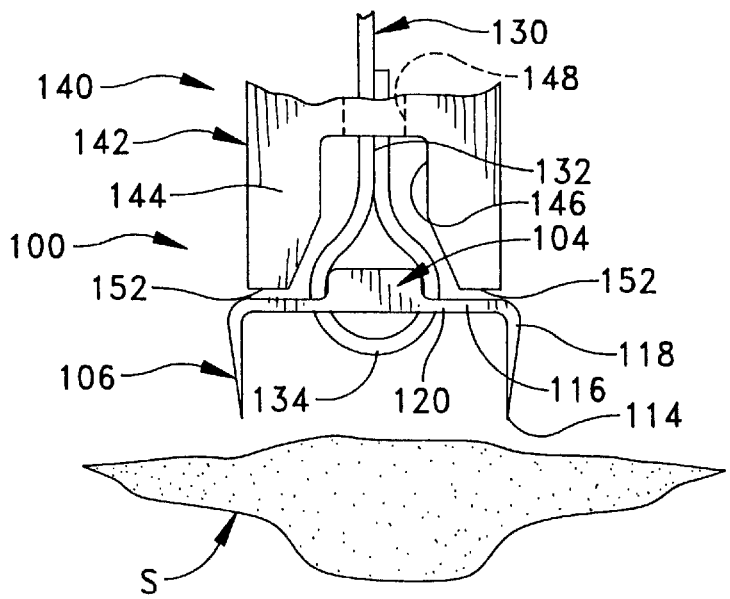
FIG. 13 is a front elevational view of the suspension clip assembly and emplacement tool of FIG. 12, with elements being shown before the suspension clip engages soft tissue.
Figure 14:
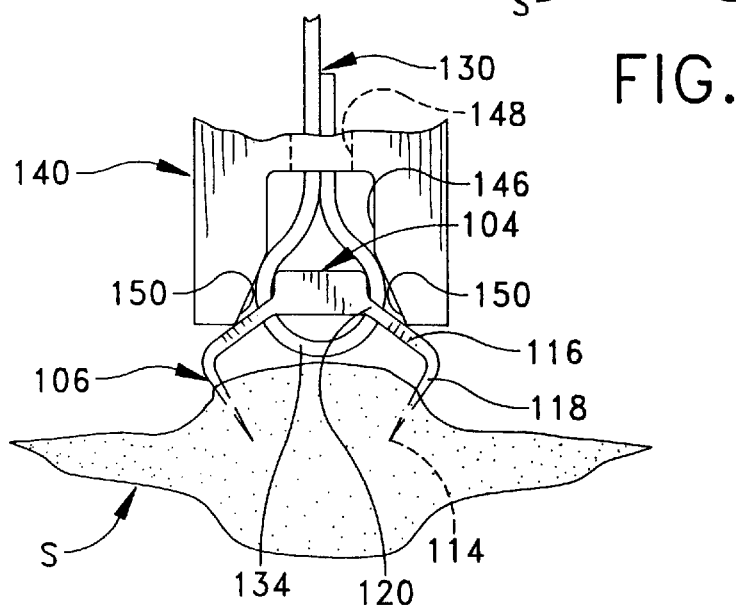
FIG. 14 is a view similar to FIG. 13, but illustrative of the emplacement tool in the process of implanting the suspension clip.
Figure 15:
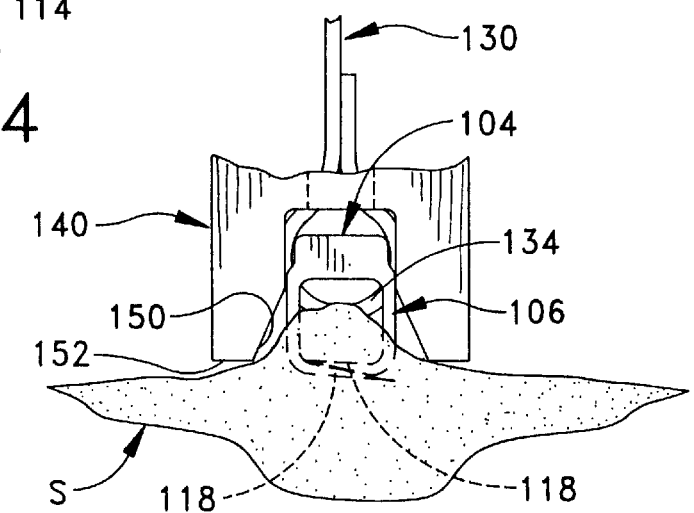
FIG. 15 is a view similar to FIG. 14, but shows the suspension clip fully implanted.

In FIGS. 12–15, there is shown a portion of an emplacement tool 140 for emplacing suspension clip assembly 100 in soft tissue. Emplacement tool 140 includes a shaft 142 having a distal end 144. The shaft's distal end 144 defines a pocket or recess 146 for receiving the suspension clip's base block 104 and the distal end 132 of strap 130 (FIGS. 14 and 15). The emplacement tool's shaft 142 defines a passageway 148 which extends lengthwise of shaft 142 and communicates with pocket 146, whereby it may receive suspension strap 130 extending from the suspension clip's base block 104. The shaft's distal end 144 also includes end surfaces 152 which are engageable with the suspension clip's leg first portions 116 (FIG. 13) so as to urge the pointed ends 114 of the legs into soft tissue S. In the pocket 146, shaft 142 defines cam surfaces 150 which are engageable with the legs 106 and 110 (FIG. 14) so as to bend each of the legs 106 at the junction 120 toward another of the legs 106, and so as to bend each of the legs 110 at the junction 120 toward another of the legs 110, whereby suspension clip 120 may grip the soft tissue S (FIGS. 14 and 15).

In operation, suspension clip 102 is placed adjacent the tissue soft tissue S which is to be grasped (FIG. 13). The emplacement tool's distal end 144 is then moved distally along the strap 130 until the tool's end surfaces 152 engage leg first portions 116. Further distal movement of tool 140 thereupon drives the legs 106 and 110 inboard into the soft tissue S (FIG. 14). Still further distal movement of tool 140 causes the tool's cam surfaces 150 to engage the leg's first portions 116 so as to cause further bending of the legs 106 and 110 until the second portions 118 of the legs are overlapped (FIG. 15) and extending in opposite directions so as to securely grasp the soft tissue S. Thereafter, the procedure is similar to that illustrated in FIGS. 9 and 9B, i.e., the strap 130 is pulled selectively taut and attached to an appropriate bodily support structure, such as bone B, by a connector means, such as an orifice, loop, snap fitting, or the like. In the case of an orifice type connector, a selected orifice in a proximal portion of the strap 130 is passed over the head of pin P in bone B so as to suspend the soft tissue in a stable condition.

The base block 104 and leg portions 118 define therebetween a shape and volume of tissue capturable by clip 102, and which can be substantially duplicated by a second clip of construction and size similar to clip 102.

In the suspension clip assembly 100 shown in FIGS. 10–15, the suspension strap's loop portion 134 is preferably arranged so as to directly engage soft tissue S (FIG. 15). In due course, the soft tissue S will adhere to loop 134 so as to securely anchor suspension clip assembly 100 to the soft tissue S. To this end, the suspension strap's loop portion 134 preferably is formed with a plurality of openings in its structure (e.g., it might be webbed) so as to enhance such tissue adhesion.

Figure 16:
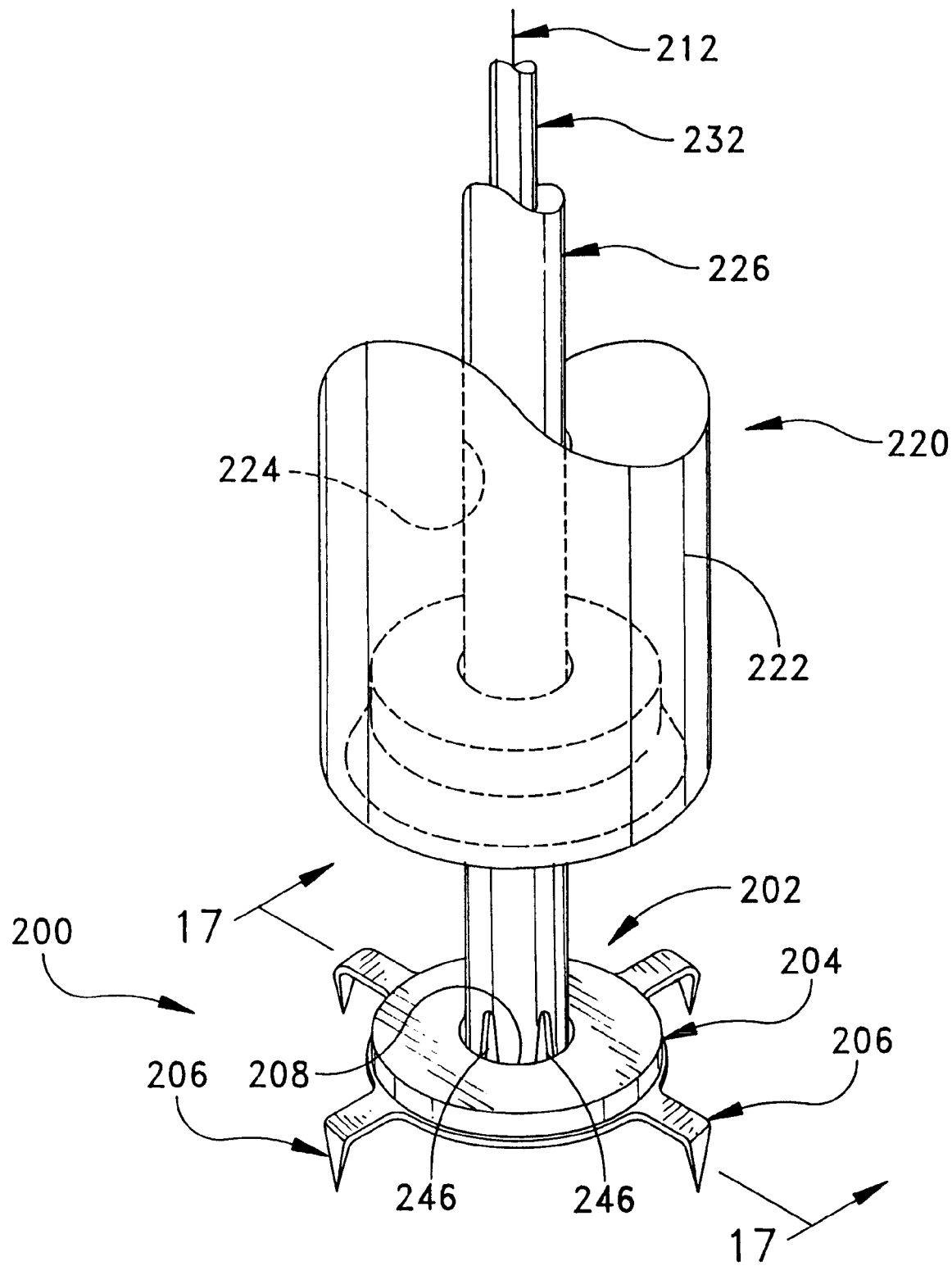
FIG. 16 is a perspective view of alternative embodiments of suspension clip, suspension clip assembly and emplacement tool.
Figure 17:
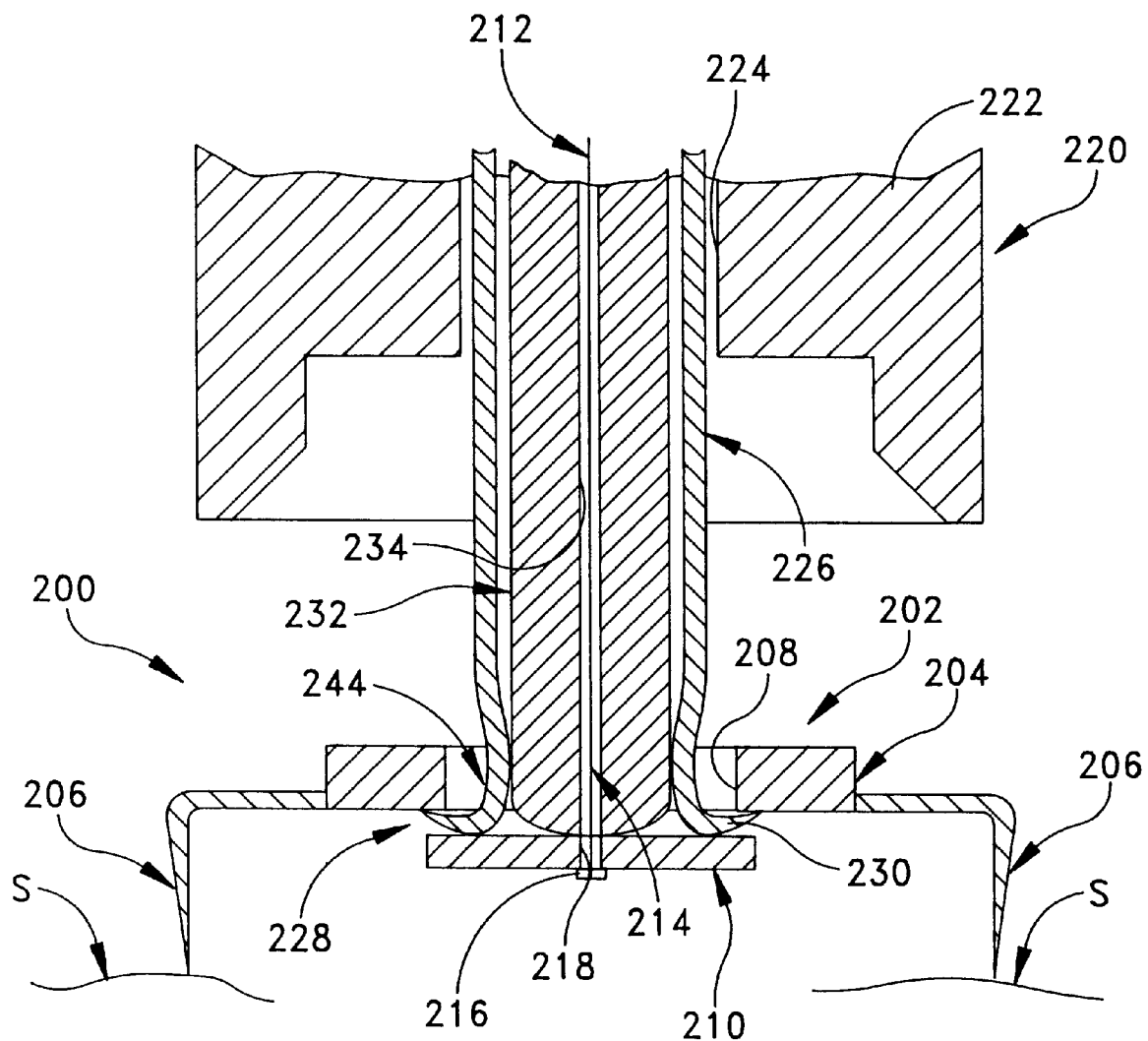
FIG. 17 is a sectional view taken along line 17—17 of FIG. 16.
Figure 21:
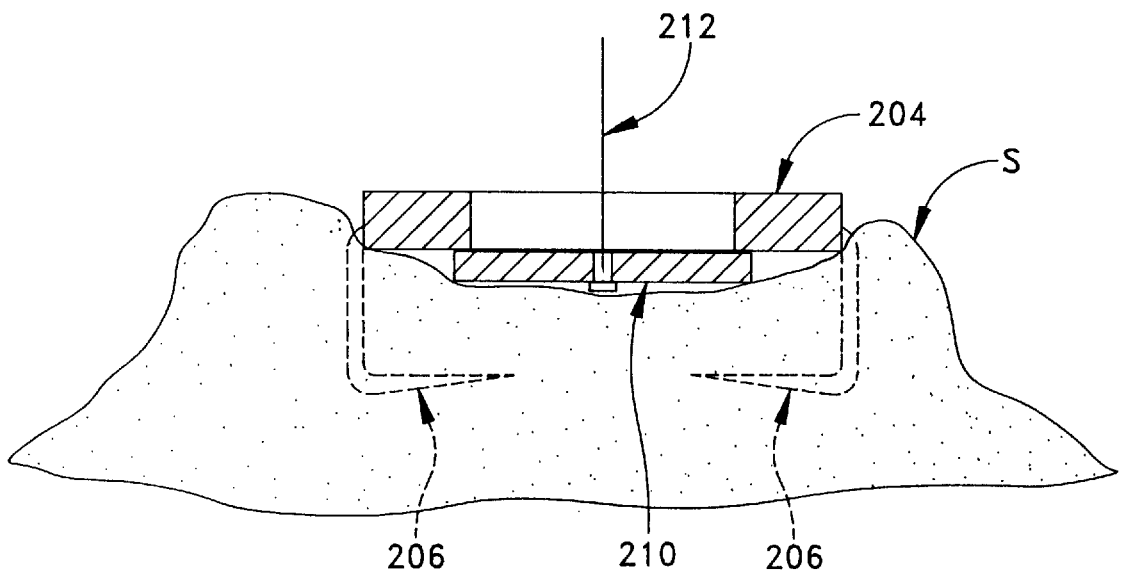
FIG. 21 is a sectional view of the suspension clip assembly of FIG. 20 secured to soft tissue.

In FIGS. 16 and 17, there is shown an alternative embodiment of suspension clip assembly 200. Suspension clip assembly 200 comprises a suspension clip 202 having a non-rectangular base block 204 and a number of pointed, bendable legs 206. Preferably base block 204 is formed so as to have a substantially circular configuration. Legs 206 are generally similar to the legs 106 and 110 previously described, in the sense that they extend outwardly and downwardly from block 204, as shown in FIG. 16. Suspension clip 202 further includes a central opening 208 extending through base block 204, and a plate 210 (FIG. 17) adapted to close the opening 208 (FIG. 21), as will hereinafter be discussed in further detail. While four legs 206 are shown in FIGS. 16 and 17, it will be apparent that additional legs (not shown) could also be disposed on block 204.

Suspension clip assembly 200 further includes a suspension strap 212, which may comprise a suture (as shown in FIGS. 16–21), wire, web, chain, or the like, and which is mounted at a distal end 214 thereof on the plate 210. In the case where the distal end of strap 212 comprises a filament-like element (e.g., the suture shown in FIGS. 16–21), the proximal end of the strap preferably comprises a web-like element (e.g., an element of the sort shown in FIGS. 4 and 9). As shown in FIG. 17, strap 212 may be mounted on the plate 210 by having a bead or body 216 fixed on the distal end 214 of the strap and extending the strap 212 through an orifice,218 formed in plate 210. Plate 210 is initially discrete from the remainder of suspension clip 202, but it is joined to the remainder of the suspension clip (FIG. 21) during use of the suspension clip assembly, as will hereinafter be described in further detail.

Referring again to FIGS. 16 and 17, an emplacement tool 220 is disclosed for emplacement of suspension clip assembly 200 in soft tissue S. Emplacement tool 220 includes a shaft 222 having a central passageway 224 extending lengthwise thereof. A tube 226 is slidably disposed within passageway 224. Tube 226 is flared outwardly at a distal end 228 thereof so as to provide an annular flange 230. Annular flange 230 is normally sized so as to have smaller diameter than internal diameter of opening 208 (FIG. 20), whereby the flange can be passed through opening 208. A core member 232 is slidably disposed within tube 226 and is provided with a central bore 234 extending lengthwise thereof. Bore 234 is adapted to receive the strap 212, which is extendible therethrough.

The engagement tool's core member 232 is sized so that when it is moved distally so as to engage a necked-down portion 244 of tube 226 (FIG. 19), core member 232 will force the necked-down portion 244 to spread outward, causing the annular flange 230 to spread. The tube 226, and particularly the necked-down portion 244 and the flange 230, is provided with open-ended slots 246 (FIG. 16) which facilitate expansion and contraction of the necked-down portion 244 and the flange 230. As a result, suspension clip assembly 200 can be held to the distal end of emplacement tool 220 (FIG. 17). At the same time, when core member 232 is moved proximally within the emplacement tool, the tube's necked-down portion 244 and flange 230 will be permitted to return to their relaxed position, such that flange 230 can pass through base block opening 208 so as to release suspension clip assembly 200 (FIG. 20).

Figure 18:
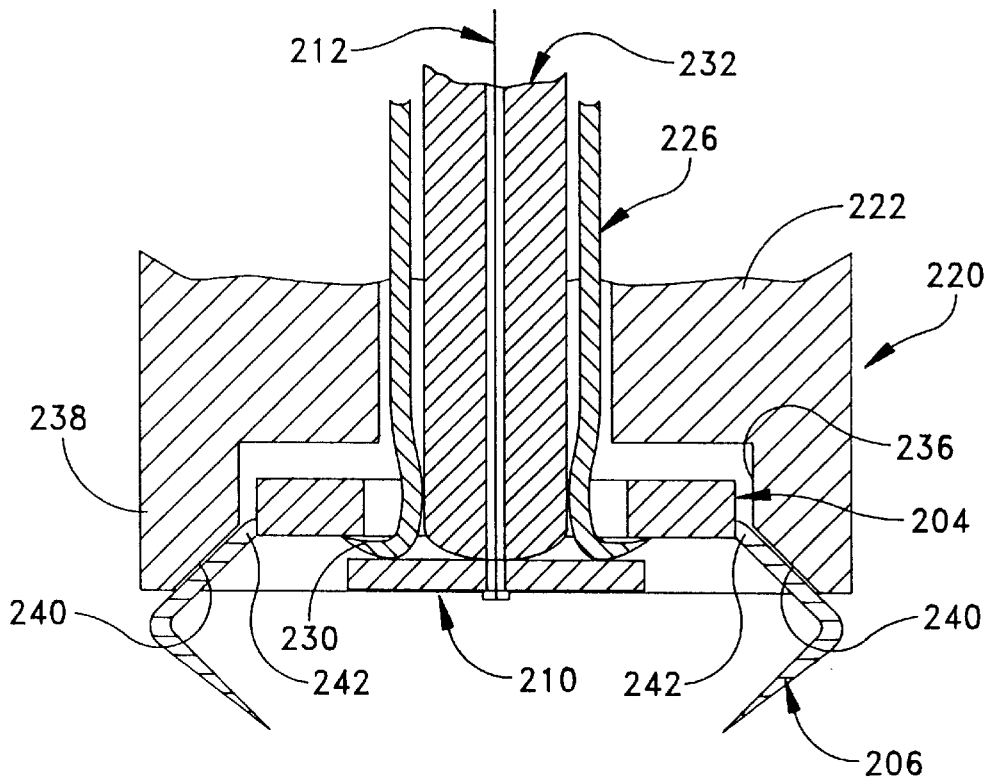
FIGS. 18–20 are views generally similar to FIG. 17, but illustrative of different operative positions.

In operation, suspension clip assembly 200 is mounted on the distal end 228 of tube 226, with suspension strap 212 extending through the core member's bore 234. Emplacement tool 220 is then maneuvered so as to bring suspension clip assembly 200 into contact with the soft tissue S which is to be grasped, as shown in FIG. 17. The emplacement tool's shaft 222 is then advanced distally along tube 226 until the suspension clip's base block 204 is received in a cavity 236 formed in a distal end 238 of shaft 222, and cam surfaces 240 disposed in cavity 236 engage clip legs 206 (FIG. 18). This action causes legs 206 to bend at their junctures 242 with base block 204 so as to pierce the soft tissue S.

Figure 19:
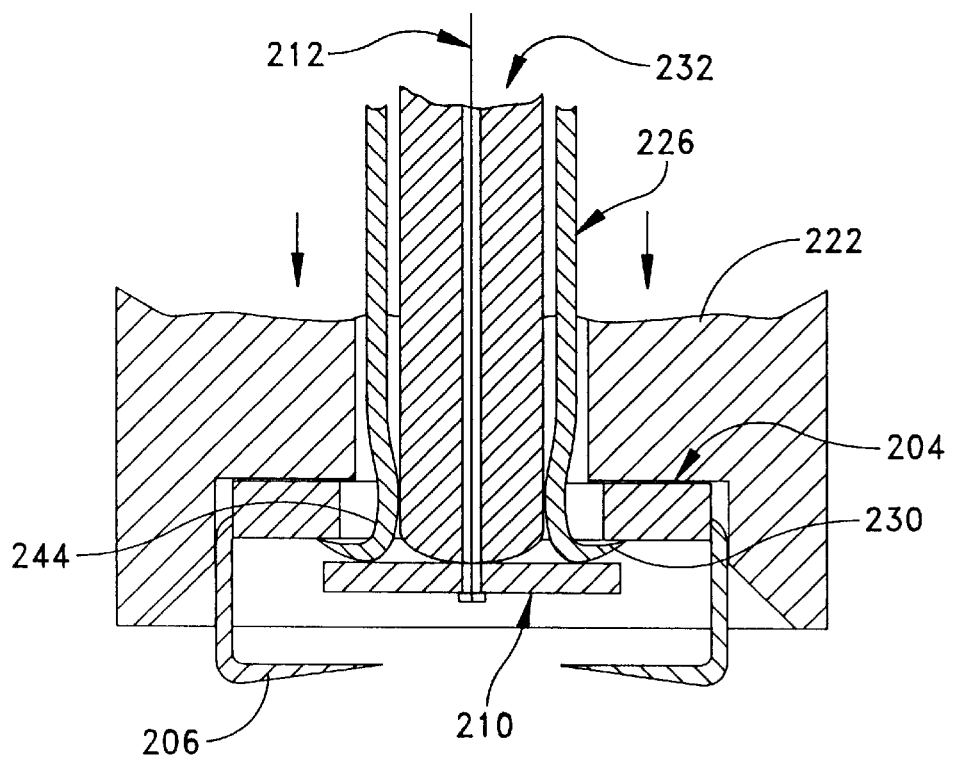

Further downward movement of the emplacement tool's shaft 222 will then drive legs 206 further inboard until their sharp tips face one another, thereby securely locking the suspension clip assembly to the soft tissue (FIG. 19).

Figure 20:
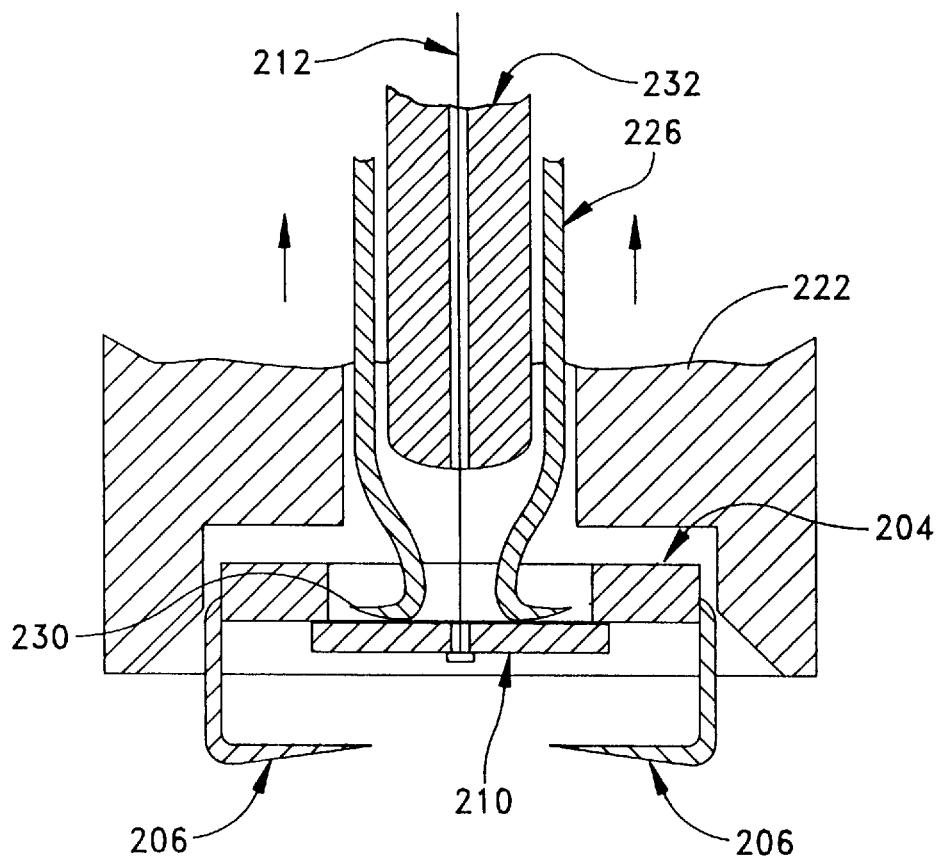

Next, core member 232 is moved proximally so as to permit flange 230 to move inboard, and then tube 226 is moved proximally so as to release suspension clip assembly 200 from the emplacement tool (FIG. 20).

Thereafter, strap 212 is drawn selectively taut, thereby keeping plate 210 up against the underside of base block 204 (FIG. 21), and then proximal end 52 of the suspension strap 212 is fixed to another body part, such as bone B, so as to suspend the soft tissue S from the bone B, in the manner generally illustrated in FIGS. 9 and 9B.

In FIGS. 22 and 23, there is shown a suspension clip assembly 300 which comprises another form of the present invention. Suspension clip assembly 300 comprises an elongated, relatively rigid body 305 having a longitudinal axis 310, and an elongated, relatively flexible suspension strap 315 attached to body 305. Suspension strap 315 in turn comprises a first, distalmost portion 320 formed out of a relatively resilient material (e.g., nylon), and a second, proximalmost portion 325 formed out of a mesh material (e.g., PTFE or Marlex). Body 305 is attached to the first, distalmost portion 320 of suspension strap 315 so that (i) the first, distalmost portion 320 of suspension strap 315 normally extends substantially perpendicular to the longitudinal axis 310 of body 305, in the manner shown in FIG. 22, and (ii) the first, distalmost portion 320 of suspension strap 315 may be bent so that at least some of the first, distalmost portion 320 of suspension strap 315 extends substantially parallel to the longitudinal axis 310 of body 305, in the manner shown in FIG. 23. On account of the foregoing, when body 305 is driven through soft tissue with at least some of the first, distalmost portion 320 of suspension strap 315 extending substantially parallel to the longitudinal axis 310 of body 305, the first, distalmost portion 320 of suspension strap 315 will thereafter cause body 305 to turn so as to restore the original perpendicular orientation of the first, distalmost portion 320 of suspension strap 315 relative to body 305. In this way, body 305 may be oriented so as to permit passage of body 305 through soft tissue whereby body 305 will reside on the far side of that soft tissue, yet will thereafter turn itself so as to bar body 305 from returning back through that soft tissue.

Preferably, suspension clip assembly 300 has its suspension strap 315 configured so that at least a portion of the second, proximalmost portion 325 of suspension strap 315 is disposed within the interior of the soft tissue when body 305 is disposed on the far side of the soft tissue. In this way the soft tissue may thereafter adhere to the mesh material which makes up the second, proximalmost portion 325 of suspension strap 315. To encourage adhesion, strap portion 325 may be coated with an adhesion-enhancing agent.

Looking still at FIG. 23, an emplacement tool 350 is preferably used to deploy suspension clip assembly 300. Emplacement tool 350 comprises a housing 355 having a pre-curved pocket 360 adjacent its distal end 365. A passageway 370 extends through housing 355 along a longitudinal axis 375 and opens on pre-curved pocket 360. A slot 376 connects passageway 370 with the region outside housing 355. An elongated shaft 378 is slidably disposed in passageway 370. Elongated shaft 378 terminates in a pointed distal end 379, whereby shaft 378 may easily penetrate tissue. Shaft 378 is sized so that it will make a close sliding fit within the housing's passageway 370, yet will be too large to fit through slot 376. Elongated shaft 378 has (i) a bore 380 extending lengthwise therethrough, and (ii) a radial slot 381 extending along the length of bore 380 and communicating with both bore 380 and the region exterior of shaft 378. In particular, radial slot 381 communicates with housing slot 376. Bore 380 is sized so as to be able to slidably receive the body 305 of the suspension clip assembly 300, with slot 381 being sized so as to permit the suspension strap 315 to pass from the body 305 disposed in bore 380 to the region exterior of shaft 378. In particular, suspension strap 315 can pass from body 305 all the way to the region exterior of housing 355 by way of shaft slot 381 and housing slot 376. A pusher 385 is slidably disposed in bore 380 and adapted to push body 305 of the suspension clip assembly 300 along bore 380 so as to expel body 305 from the distal end 379 of shaft 378.

The emplacement tool's pre-curved pocket 360 is configured so that when a piece of soft tissue is disposed in pre-curved pocket 360, and when the body 305 of a suspension clip assembly 300 is carried through the tissue by elongated shaft 378 and thereafter ejected from bore 380 by pusher 385, suspension clip assembly 300 will be properly attached to the soft tissue. To this end, pre-curved pocket 360 is formed with a dimension L (FIG. 23) which reflects the desired length of penetration of suspension clip assembly 300 through the soft tissue, and with a dimension T (FIG. 23) which reflects the desired depth of penetration of the suspension clip assembly 300 into the soft tissue.

Figure 24:
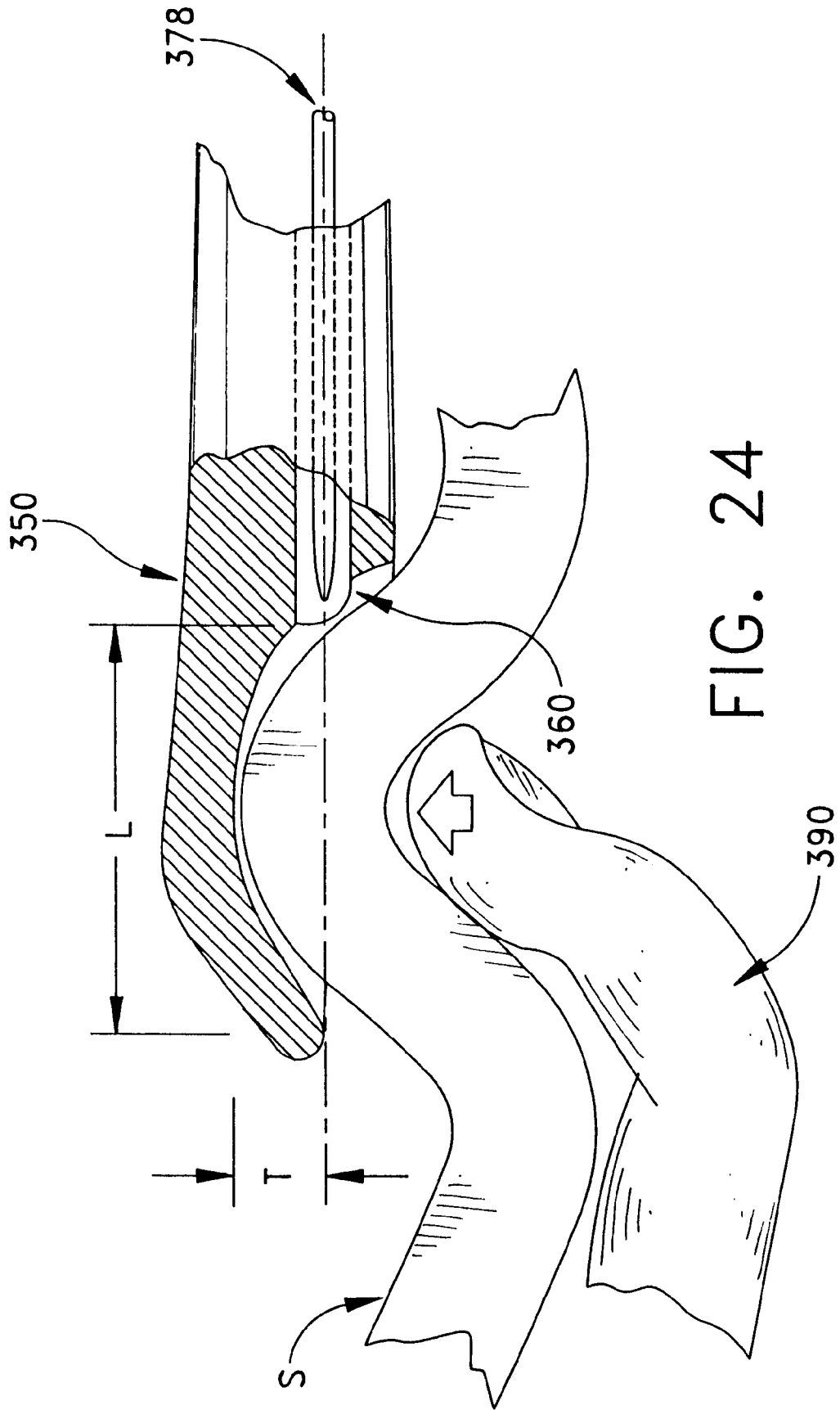
FIG. 24 is a schematic partial side view showing the emplacement tool of FIG. 23 deploying the suspension clip assembly of FIG. 22 in soft tissue.

Looking still at FIG. 23, suspension clip assembly 300 and emplacement tool 350 are preferably used as follows. First, suspension clip assembly 300 is loaded into emplacement tool 350 in the manner shown in FIG. 23, i.e., so that body 305 is disposed in shaft 378, shaft 378 is disposed in passageway 370, suspension strap 315 extends out through slots 381 and 376, and pusher 385 engages (or approximately engages) the proximal end of body 305. Emplacement tool 350 is then maneuvered so that a piece of soft tissue S (FIG. 24) projects up into the tool's pre-curved pocket 360. Depending on the procedure being conducted, the surgeon's finger 390 or a surgical tool (not shown) may be used to help force soft tissue S up into pre-curved pocket 360. By way of example, during a bladder neck suspension procedure, or during a prolapsed uterus suspension procedure, the surgeon's finger 390 might be used to force the patient's vaginal wall up into the tool's pre-curved pocket 360. Next, shaft 378 is passed through soft tissue S, until its sharp distal tip 379 emerges on the far side of the soft tissue. Plunger 385 (FIG. 23) is then used to eject body 305 out of shaft 378, whereby body 305 will "right itself" on the far side of the tissue so as to prevent body 305 from being withdrawn back through the tissue. At the same time, suspension strap 315 will extend through the soft tissue. The second, proximalmost portion 325 of suspension strap 315 may then be attached to a bone B, or other internal bodily support structure, in a manner analogous to that shown in FIGS. 9 and 9B.

Alternatively, the first distalmost portion 320 of strap 315 may be of relatively flexible material, rather than resilient material, provided tool 350 is provided with means (not shown) for turning body 305 on the far side of the tissue. In such instance, the distalmost portion 320 permits body 305 to be turned, rather than causing such turning. Of course, the first distalmost portion 320 cannot be of such elasticity as to adversely affect the desired tension on the supported tissue.

The pocket 360 and the shaft 378, or a hypothetical extension of passageway 370, define a volume substantially equal to a selected volume of tissue to be captured by the clip and which may be substantially duplicated by other clips of similar structure and size emplaced by tool 350.

Figure 25:
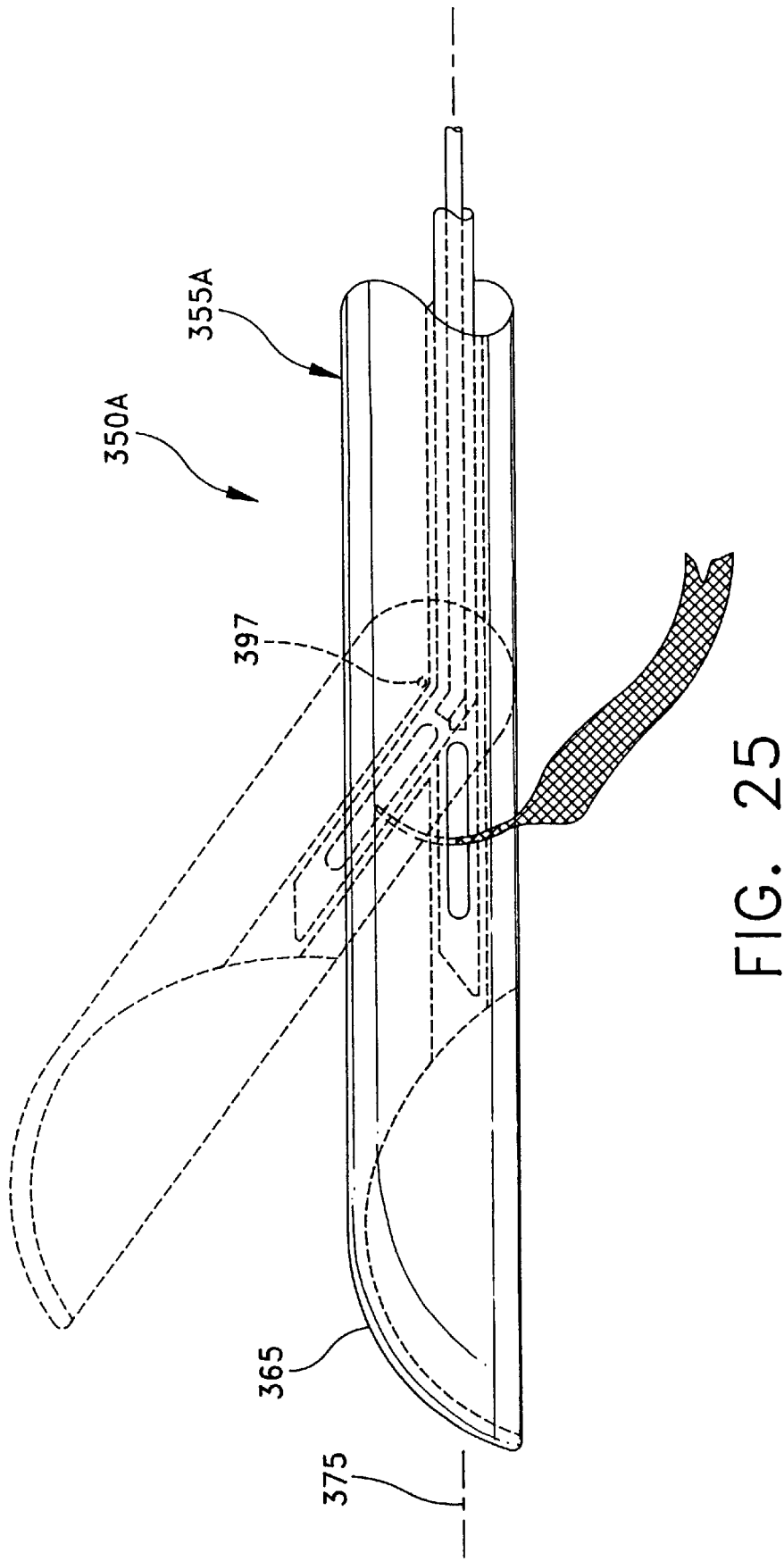
FIG. 25 is a partial side view showing an alternative form of emplacement tool for deploying the suspension clip assembly of FIG. 22.

In some cases it may not be possible to approach the target tissue from the ideal angle, due to anatomical considerations. In this situation, an emplacement tool 350A (FIG. 25) might be used. Tool 350A is identical to tool 350, except that shaft 355A has its distal end 365A connected to the remainder of the shaft by means of a pivot connection 397. Alternatively, shaft 355A may be of a flexible material. In this way tool 350A can assume a desired orientation for proper receipt of soft tissue S in precurved pocket 360, regardless of the angle of entry of the emplacement tool into the body. Of course, with this embodiment, shaft 378 and pusher 385 should be formed so as to be somewhat flexible so that they can operate even when the distal end 365A of shaft 355A is deflected off longitudinal axis 375. Preferably pivot connection 397 includes a spring return (not shown), whereby the distal end 365A of shaft 355A will normally be aligned with longitudinal axis 375.

Figure 26:
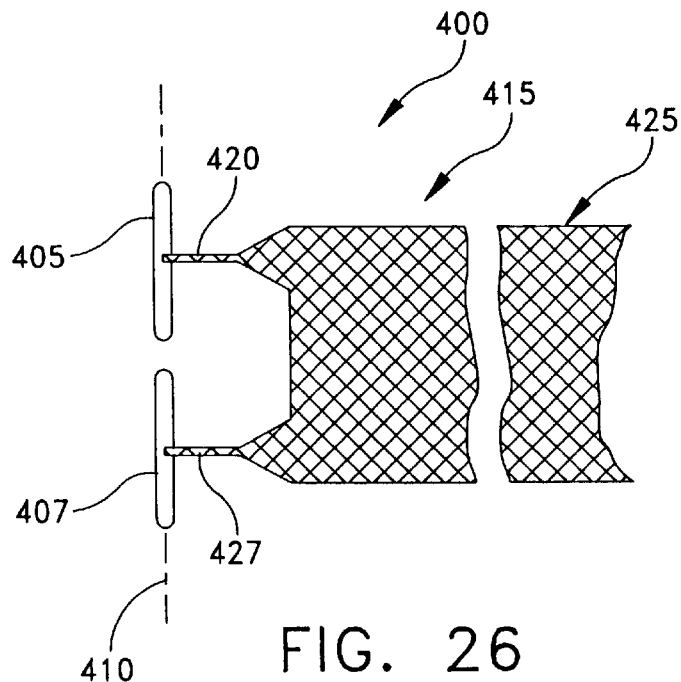
FIG. 26 is a partial top view of an alternative embodiment of suspension clip assembly.
Figure 27:
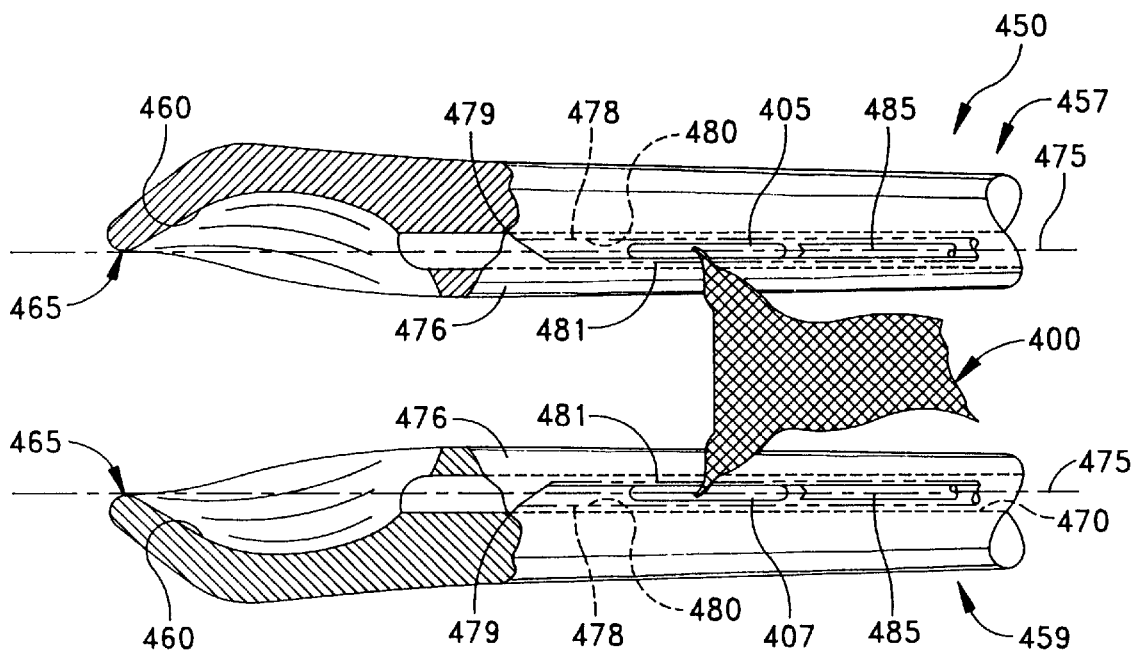
FIG. 27 is a partial top view, partly in section, of the suspension clip assembly of FIG. 26 shown loaded in a appropriate emplacement tool.

In FIGS. 26 and 27, there is shown a suspension clip assembly 400 which comprises another form of the present invention. Suspension clip assembly 400 comprises elongated, relatively rigid first and second bodies 405, 407, each having a longitudinal axis 410, and an elongated, relatively flexible suspension strap 415 attached to bodies 405, 407. Suspension strap 415, in turn, comprises a first distalmost portion 420 and a second distalmost portion 422 formed of a relatively resilient material (e.g., nylon), and a proximalmost portion 425 formed of a mesh material (e.g., PTFE or Marlex). Bodies 405, 407 are attached, respectively, to the distalmost portions 420, 422 of suspension strap 415 such that (i) the first and second distalmost portions 420, 422 of suspension strap 415 normally extend, respectively, substantially perpendicular to the longitudinal axis 410 of bodies 405, 407 in the manner shown in FIG. 26, and (ii) the first and second distalmost portions 420, 422 of suspension strap 415 may be bent so that at least some of the first and second distalmost portions 420, 422 of suspension strap 415 may be extended substantially parallel to the longitudinal axes 410 of bodies 405, 407, in the manner shown in FIG. 27. On account of the foregoing, when bodies 405, 407 are driven through soft tissue with at least some of the first and second distalmost portions 420, 422 of suspension strap 415 extending substantially parallel to the longitudinal axes 410 of bodies 405, 407, the first and second distalmost portions 420, 422 of suspension strap 415 will thereafter cause bodies 405, 407 to turn to restore the original perpendicular orientation of the first and second distalmost portions 420, 422 of suspension strap 415 relative to bodies 405, 407. In this way, bodies 405, 407 are oriented to permit passage of bodies 405, 407 through soft tissue, whereby bodies 405, 407 reside on a far side of the soft tissue, yet will thereafter turn themselves so as to bar bodies 405, 407 from returning back through the soft tissue.

Preferably, suspension strap 415 of suspension clip assembly 400 is configured such that at least a portion of the proximalmost portion 425 of suspension strap 415 is disposed within the interior of the soft tissue when body 405 is disposed on the far side of the piece of soft tissue. In this way, the soft tissue may thereafter adhere to the mesh material which makes up the second, proximalmost portion 425 of suspension strap 415.

Looking still at FIG. 27, an emplacement tool 450 preferably is used to deploy suspension clip assembly 400. Emplacement tool 450 comprises a housing 455 having first and second housing portions 457, 459, each having a curved pocket 460 adjacent a distal end 465 thereof. A passageway 470 extends through each housing portion 457, 459 along a longitudinal axis 475 and opens into one of the curved pockets 460. In each housing portion, 457, 459, a slot 476 connects passageway 470 with a region outside housing 455. An elongated shaft 478 is slidably disposed in each passageway 470. Elongated shafts 478 each terminate in a pointed distal end 479 whereby shafts 478 may easily penetrate tissue. Shafts 478 are sized to make a close sliding fit within the housing passageways 470, yet are too large to fit through slots 476. Elongated shafts 478 have (i) a bore 480 extending lengthwise therethrough, and (ii) a radial slot 481 extending along the length of bore 480 and communicating with both bore 480 and the region exterior of shaft 478. In particular, radial slots 481 communicate with housing slots 476. Bores 480 are sized to be able to slidably receive the respective bodies 405, 407 of the suspension clip assembly 400, with slots 481 sized to permit the suspension strap 415 to pass from the bodies 405, 407 disposed in bores 480 to the region exterior of shafts 478. In particular, suspension strap 415 can pass from bodies 405, 407 all the way to the region exterior of housing 455 by way of shaft slots 481 and housing slots 476. A pusher 485 is slidably disposed in each bore 480 and adapted to push bodies 405, 407 of the suspension clip assembly 400 along bores 480 to expel bodies 405, 407 from the distal ends 479 of shafts 478.

The curved pockets 460 of the emplacement tool are each configured such that when a piece of soft tissue is disposed in a curved pocket 460, and when the bodies 405, 407 of a suspension clip assembly 400 are carried through the tissue by elongated shafts 478 and, thereafter, ejected from bores 480 by pushers 485, suspension clip assembly 400 is properly attached to the soft tissue. To this end, curved pockets 460 are each formed with a dimension L (FIG. 23) which reflects the desired length of penetration of suspension clip assembly 400 through the soft tissue, and with a dimension T (FIG. 23) which reflects the desired depth of penetration of the suspension clip assembly 400 into the soft tissue.

Emplacement tool 450 is used in much the same manner as emplacement tool 350, described hereinabove, but provides the extra security of doubling the number of bodies 405, 407, as opposed to the single body 305 described hereinabove.

There is thus provided a novel soft tissue suspension clip and suspension clip assembly, and an emplacement tool for the suspension clip assembly, and a method for suspending soft tissue from an appropriate bodily support structure.

There are further provided tissue suspension clips which facilitate grasping of substantially the same amount of tissue each time used, and a tool which facilitates placement of clips so as to grasp substantially equal amounts of tissue each time used.

There is still further provided a suspension clip assembly in which bodily adhesion, over time, operates to increase the attachment between the suspension clip assembly and the suspended tissue.

There is still further provided a suspension clip assembly and method which include relatively easy fine-tuning of suspension tension, immediately upon completion of the suspension operation and before closing, and/or subsequently, after the passage of time has caused a change in the tension on the suspension strap.

It is to be understood that the present invention is by no means limited to the particular constructions and methods herein disclosed and/or shown in the drawings, but also comprises any modifications or equivalents within the scope of the claims. For example, while it is contemplated that the suspension clip assembly will be packaged and used as a unit, it will be apparent that the suspension clip and strap could be discrete units which are joined together just prior to, or during, the operative procedure.

Furthermore, while the foregoing description of suspension clips, suspension clip assemblies, emplacement tools, and methods have been illustrated in the context of a bladder neck suspension, and while it is anticipated that the invention will find utility in the effecting a bladder neck suspension, it will be apparent that the same devices and methods are equally applicable to a wide variety of other suspension environments as, for example, in drawing various internal organs from others so as to prevent the formation of adhesions therebetween.

What is claimed is:

1. A method for effecting suspension of soft tissue from an appropriate bodily support structure, said method comprising the steps of:

providing a suspension clip assembly comprising an elongated, relatively rigid body having a longitudinal axis, and an elongated, relatively flexible suspension strap attached to said body, said suspension strap comprising a first distalmost portion formed out of a relatively flexible material, and a second, proximalmost portion formed out of a mesh material, said body being attached to said first, distalmost portion of said suspension strap so that (i) said first, distalmost portion of said suspension strap normally extends substantially perpendicular to said longitudinal axis of said body, and (ii) said first, distalmost portion of said suspension strap may be bent so that at least some of said first, distalmost portion of said suspension strap extends substantially parallel to said longitudinal axis of said body, whereby when said body is driven through soft tissue with at least some of said first, distalmost portion of said suspension strap extending substantially parallel to said longitudinal axis of said body, said first, distalmost portion of said suspension strap will thereafter permit said body to turn so as to restore the original perpendicular orientation of said first, distalmost portion of said suspension strap relative to said body;

passing the body of the suspension clip assembly through the soft tissue so that the body resides in the far side of the soft tissue and the suspension strap extends through the soft tissue; and fixing said second, proximalmost portion of said suspension strap to the appropriate bodily support structure, whereby to draw the soft tissue toward the bodily support structure.

2. A method for effecting suspension of soft tissue from an appropriate bodily support structure, said method comprising the steps of:

providing a suspension clip assembly comprising a first elongated relatively rigid body having a first longitudinal axis; a second elongated relatively rigid body having a second longitudinal axis; an elongated relatively flexible suspension strap attached to said first and second bodies; said suspension strap comprising first and second distalmost portions of relatively flexible material, and a proximalmost portion of a mesh material; said first body being attached to said first distalmost portion of said suspension strap such that (i) said first distalmost portion of said suspension strap normally extends substantially perpendicular to said first longitudinal axis, and (ii) said first distalmost portion of said suspension strap is bendable so that at least some of said first distalmost portion of said suspension strap is extendible substantially parallel to said first longitudinal axis; said second body being attached to said second distalmost portion of said suspensions strap such that (i) said second distalmost portion of said suspension strap normally extends substantially perpendicular to said second longitudinal axis, and (ii) said second distalmost portion of said suspension strap is bendable so that at least some of said second distalmost portion of said suspension strap is extendible substantially parallel to said second longitudinal axis; whereby when said first and second bodies are driven through soft tissue with at least some of said first and second distalmost portions of said suspension strap extending substantially parallel to said first and second longitudinal axes, respectively, said first and second distalmost portions of said suspension strap permit said first and second bodies, respectively, to turn to restore the original perpendicular orientation of said first distalmost portion of said suspension strap relative to said first body and said second distalmost portion of said suspension strap relative to said second body;

passing the bodies of the suspension clip assembly through the soft tissue such that the bodies reside in a far side of the soft tissue and the suspension strap extends through the soft tissue; and fixing the proximalmost portion of the suspension strap to the support structure;

whereby to draw the soft tissue toward the support structure.

3. A suspension clip assembly comprising:

a first elongated relatively rigid body having a first longitudinal axis;

a second elongated relatively rigid body having a second longitudinal axis;

an elongated relatively flexible suspension strap attached to said first and second bodies;

said suspension strap comprising first and second distalmost portions of relatively flexible material, and a proximalmost portion of a mesh material;

said first body being attached to said first distalmost portion of said suspension strap such that (i) said first distalmost portion of said suspension strap normally extends substantially perpendicular to said first longitudinal axis, and (ii) said first distalmost portion of said suspension strap is bendable so that at least some of said first distalmost portion of said suspension strap is extendible substantially parallel to said first longitudinal axis;

said second body being attached to said second distalmost portion of said suspension strap such that (i) said second distalmost portion of said suspension strap normally extends substantially perpendicular to said second longitudinal axis, and (ii) said second distalmost portion of said suspension strap is bendable so that at least some of said second distalmost portion of said suspension strap is extendible substantially parallel to said second longitudinal axis;

whereby when said first and second bodies are driven through soft tissue with at least some of said first and second distalmost portions of said suspension strap extending substantially parallel to said first and second longitudinal axes, respectively, said first and second distalmost portions of said suspension strap permit said first and second bodies, respectively, to turn so as to restore the original perpendicular orientation of said first distalmost portion of said suspension strap relative to said first body and said second distalmost portion of said suspension strap relative to said second body.

4. A suspension clip assembly according to claim 3 wherein said suspension strap is configured such that at least a portion of said proximalmost portion of said suspension strap is disposed within the piece of soft tissue when said first and second bodies are disposed on a far side of the piece of soft tissue.

5. A suspension clip assembly comprising:

a suspension strap having a distal end and a proximal end; and a clip fixed to said distal end of said strap and adapted for attachment to tissue to be suspended;

said suspension strap being of a mesh-like material, whereby said distal end of said strap is subject to adhesion to said tissue; and said proximal end of said strap is adapted for hanging on a pin extending from a support body part.

6. A suspension clip assembly for suspending soft tissue from an appropriate bodily support structure, said assembly comprising:

a suspension clip having means thereon for penetrating the soft tissue; and a suspension strap having a proximal end and a distal end, said suspension strap being mounted at said distal end thereof to said suspension clip and extending therefrom;

said suspension strap having means thereon proximate said proximal end thereof for attaching said suspension strap to the appropriate bodily support structure.

7. A suspension clip assembly comprising:

an elongated, relatively rigid body having a longitudinal axis; and an elongated, relatively flexible suspension strap attached to said body;

said suspension strap comprising a first distalmost portion formed out of a relatively flexible material, and a second, proximalmost portion formed out of a mesh material;

said body being attached to said first, distalmost portion of said suspension strap so that (i) said first, distalmost portion of said suspension strap normally extends substantially perpendicular to said longitudinal axis of said body, and (ii) said first, distalmost portion of said suspension strap may be bent so that at least some of said first, distalmost portion of said suspension strap extends substantially parallel to said longitudinal axis of said body;

whereby when said body is driven through soft tissue with at least some of said first, distalmost portion of said suspension strap extending substantially parallel to said longitudinal axis of said body, said first, distalmost portion of said suspension strap will thereafter permit said body to turn so as to restore the original perpendicular orientation of said first, distalmost portion of said suspension strap relative to said body.

* * * * *